(12) United States Patent
Cheng et al.

(10) Patent No.: US 10,799,097 B2
(45) Date of Patent: *Oct. 13, 2020

(54) ENDOSCOPE SYSTEM INCLUDING A RESILIENT RESERVOIR

(71) Applicant: Gyrus ACMI, Inc., Southborough, MA (US)

(72) Inventors: Ming J. Cheng, W. Warwick, RI (US); David C. Church, Millington, TN (US); Daniel R. Goldberg, Memphis, TN (US); Gregory S. Konstorum, Stamford, CT (US); J. Andrew Willhite, Memphis, TN (US)

(73) Assignee: Gyrus Acmi, Inc., Southborough, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/002,498

(22) Filed: Jun. 7, 2018

(65) Prior Publication Data

US 2018/0279861 A1 Oct. 4, 2018

Related U.S. Application Data

(60) Continuation of application No. 15/095,651, filed on Apr. 11, 2016, now Pat. No. 10,022,040, which is a
(Continued)

(51) Int. Cl.
*A61B 1/00* (2006.01)
*A61B 1/015* (2006.01)
(Continued)

(52) U.S. Cl.
CPC .......... *A61B 1/015* (2013.01); *A61B 1/00068* (2013.01); *A61B 1/00119* (2013.01);
(Continued)

(58) Field of Classification Search
None
See application file for complete search history.

(56) References Cited

U.S. PATENT DOCUMENTS

| 1,555,003 A | 9/1925 | Greenberg et al. |
| 2,112,056 A | 3/1938 | Wappler |
| (Continued) | | |

FOREIGN PATENT DOCUMENTS

| CN | 1719997 A | 1/2006 |
| CN | 101188966 A | 5/2008 |
| (Continued) | | |

OTHER PUBLICATIONS

US 5,772,579 A, 06/1998, Reisdorf (withdrawn)
(Continued)

*Primary Examiner* — Timothy J Neal
(74) *Attorney, Agent, or Firm* — Schwegman Lundberg & Woessner, P.A.

(57) ABSTRACT

A system comprising: (a) a sheath configured to receive all or a portion of an endoscope; (b) an irrigation line connecting the sheath to an irrigation source; (c) a suction line connecting the sheath to a suction source; and (d) a control module located between the sheath, and the irrigation source and the suction source and controls flow of irrigation fluid from the irrigation source to the sheath and movement of suction between the suction source and the sheath; wherein the irrigation source is connected to a resilient reservoir that is located within the control module and movement of the control module compresses the resilient reservoir moving irrigation fluid from the resilient reservoir to the sheath so that the irrigation fluid assists in cleaning the endoscope, and wherein the control module includes a valve and compres-
(Continued)

sion of the resilient reservoir initiates movement of the valve so that the valve opens and suction from the suction line is applied to the sheath.

19 Claims, 6 Drawing Sheets

Related U.S. Application Data division of application No. 14/497,815, filed on Sep. 26, 2014, now Pat. No. 9,332,894.

(60) Provisional application No. 61/882,652, filed on Sep. 26, 2013.

(51) Int. Cl.
*A61B 90/70* (2016.01)
*A61B 1/06* (2006.01)
*A61B 1/12* (2006.01)

(52) U.S. Cl.
CPC ...... *A61B 1/00135* (2013.01); *A61B 1/00142* (2013.01); *A61B 1/06* (2013.01); *A61B 1/126* (2013.01); *A61B 90/70* (2016.02); *A61B 1/00128* (2013.01); *A61B 2090/701* (2016.02)

(56) References Cited

U.S. PATENT DOCUMENTS

| | | |
|---|---|---|
| 3,071,129 A | 1/1963 | Wasserman |
| 3,321,265 A | 5/1967 | Serge et al. |
| 3,572,325 A | 3/1971 | Bazell et al. |
| 3,592,199 A | 7/1971 | Ostensen et al. |
| 3,610,478 A | 10/1971 | Johnston |
| 3,659,423 A | 5/1972 | Lair et al. |
| 3,675,641 A | 7/1972 | Fiore |
| 3,689,083 A | 9/1972 | Greenawalt |
| 3,903,877 A | 9/1975 | Terada |
| 3,969,824 A | 7/1976 | Widen et al. |
| 4,254,762 A | 3/1981 | Yoon |
| 4,281,646 A | 8/1981 | Kinoshita |
| 4,312,375 A | 1/1982 | Leinemann |
| 4,525,220 A | 6/1985 | Sasa et al. |
| 4,548,197 A | 10/1985 | Kinoshita |
| 4,579,597 A | 4/1986 | Sasa et al. |
| 4,593,682 A | 6/1986 | Heckele |
| 4,646,722 A | 3/1987 | Silverstein et al. |
| 4,667,656 A | 5/1987 | Yabe |
| 4,756,303 A | 7/1988 | Kawashima et al. |
| 4,850,342 A | 7/1989 | Hashiguchi et al. |
| 4,907,395 A | 3/1990 | Opie et al. |
| 4,991,565 A | 2/1991 | Takahashi et al. |
| 5,027,792 A | 7/1991 | Meyer |
| 5,050,585 A | 9/1991 | Takahashi |
| 5,167,220 A | 12/1992 | Brown |
| 5,170,774 A | 12/1992 | Heckele |
| 5,176,645 A | 1/1993 | Guerrero |
| 5,178,606 A | 1/1993 | Ognier et al. |
| 5,199,417 A | 4/1993 | Muller et al. |
| 5,207,213 A | 5/1993 | Auhll et al. |
| 5,225,001 A | 7/1993 | Manni et al. |
| 5,237,984 A | 8/1993 | Williams et al. |
| 5,261,889 A | 11/1993 | Laine et al. |
| 5,269,756 A | 12/1993 | Dryden |
| 5,313,934 A | 5/1994 | Wiita et al. |
| 5,328,458 A | 7/1994 | Sekino et al. |
| 5,354,267 A | 10/1994 | Niermann et al. |
| 5,377,668 A | 1/1995 | Ehmsen et al. |
| 5,386,817 A | 2/1995 | Jones |
| 5,408,991 A | 4/1995 | Iida et al. |
| 5,413,092 A | 5/1995 | Williams, III et al. |
| 5,419,309 A | 5/1995 | Biehl |
| 5,419,310 A | 5/1995 | Frassica et al. |
| 5,439,022 A | 8/1995 | Summers et al. |
| 5,447,148 A | 9/1995 | Oneda et al. |
| 5,486,155 A | 1/1996 | Muller et al. |
| 5,505,707 A | 4/1996 | Manzie et al. |
| 5,509,892 A | 4/1996 | Bonnet |
| 5,514,074 A | 5/1996 | Yabe et al. |
| 5,518,501 A | 5/1996 | Oneda et al. |
| 5,551,448 A | 9/1996 | Matula et al. |
| 5,554,100 A | 9/1996 | Peck et al. |
| 5,554,112 A | 9/1996 | Walbrink et al. |
| 5,556,258 A | 9/1996 | Lange et al. |
| 5,575,756 A | 11/1996 | Karasawa et al. |
| 5,593,404 A | 1/1997 | Costello et al. |
| 5,630,795 A | 5/1997 | Kuramoto et al. |
| 5,647,840 A | 7/1997 | D'amelio et al. |
| 5,662,588 A | 9/1997 | Iida |
| 5,681,262 A | 10/1997 | Isse |
| 5,685,823 A | 11/1997 | Ito et al. |
| 5,690,605 A | 11/1997 | Hamlin et al. |
| 5,695,448 A | 12/1997 | Kimura et al. |
| 5,697,888 A | 12/1997 | Kobayashi et al. |
| 5,700,236 A | 12/1997 | Sauer et al. |
| 5,702,348 A | 12/1997 | Harhen |
| 5,733,245 A | 3/1998 | Kawano |
| 5,735,792 A | 4/1998 | Vanden et al. |
| 5,779,625 A | 7/1998 | Suzuki et al. |
| 5,785,689 A | 7/1998 | De Toledo et al. |
| 5,792,045 A | 8/1998 | Adair |
| 5,797,836 A | 8/1998 | Lucey et al. |
| 5,823,940 A | 10/1998 | Newman |
| 5,944,654 A | 8/1999 | Crawford |
| 5,989,183 A | 11/1999 | Reisdorf et al. |
| 6,110,103 A | 4/2000 | Donofrio |
| 6,126,592 A | 10/2000 | Proch et al. |
| 6,181,442 B1 | 1/2001 | Ogura et al. |
| 6,196,967 B1 | 3/2001 | Lim et al. |
| 6,282,442 B1 | 8/2001 | DeStefano et al. |
| 6,340,344 B1 | 1/2002 | Christopher |
| 6,354,813 B1 | 3/2002 | Laing |
| 6,447,446 B1 | 9/2002 | Smith et al. |
| 6,478,731 B2 | 11/2002 | Speier et al. |
| 6,558,379 B1 | 5/2003 | Batchelor et al. |
| 6,645,140 B2 | 11/2003 | Brommersma |
| 6,652,484 B1 | 11/2003 | Hunckler et al. |
| 6,824,544 B2 | 11/2004 | Boebel et al. |
| 6,911,005 B2 | 6/2005 | Ouchi et al. |
| 7,160,247 B2 | 1/2007 | Deppmeier et al. |
| 7,192,396 B2 | 3/2007 | Boulais |
| 7,252,110 B2 | 8/2007 | Semeia |
| 7,270,647 B2 | 9/2007 | Karpowicz et al. |
| 7,413,542 B2 | 8/2008 | Kucklick et al. |
| 7,708,689 B2 | 5/2010 | Deppmeier et al. |
| 7,736,301 B1 | 6/2010 | Webler et al. |
| 7,758,497 B2 | 7/2010 | Hem |
| 7,766,819 B2 | 8/2010 | Matsumoto |
| 7,811,228 B2 | 10/2010 | Adams |
| 7,942,814 B2 | 5/2011 | Remijan et al. |
| 8,001,984 B2 | 8/2011 | Sasaki |
| 8,029,438 B2 | 10/2011 | Hagihara et al. |
| 8,047,215 B1 | 11/2011 | Sasaki |
| 8,066,660 B2 | 11/2011 | Gregersen et al. |
| 8,079,952 B2 | 12/2011 | Fujimoto |
| 8,092,415 B2 | 1/2012 | Moehle et al. |
| 8,231,574 B2 | 7/2012 | Haack et al. |
| 8,231,658 B2 | 7/2012 | Oskin et al. |
| 8,337,470 B2 | 12/2012 | Prasad et al. |
| 8,393,328 B2 | 3/2013 | Angel et al. |
| 8,394,013 B2 | 3/2013 | Ichimura |
| 8,409,109 B2 | 4/2013 | Tiesma et al. |
| 8,419,624 B2 | 4/2013 | James et al. |
| 8,663,090 B2 | 3/2014 | Fujimoto |
| 8,870,752 B2 | 10/2014 | Avitsian et al. |
| 8,888,689 B2 | 11/2014 | Poll et al. |
| 8,911,415 B2 | 12/2014 | Knapp |
| 8,915,842 B2 | 12/2014 | Weisenburgh, II et al. |
| 8,978,657 B2 | 3/2015 | Sandmore et al. |
| 9,078,562 B2 | 7/2015 | Poll et al. |
| 9,144,664 B2 | 9/2015 | Jacobsen et al. |
| 9,155,453 B2 | 10/2015 | Kumar et al. |
| 9,332,894 B2 * | 5/2016 | Cheng ............... A61B 1/06 |

(56) References Cited

U.S. PATENT DOCUMENTS

| | | |
|---|---|---|
| 10,022,040 B2 | 7/2018 | Cheng et al. |
| 10,028,644 B2 | 7/2018 | Konstorum et al. |
| 10,098,524 B2 | 10/2018 | Cheng et al. |
| 10,478,052 B2 | 11/2019 | Konstorum et al. |
| 10,631,717 B2 | 4/2020 | Cheng et al. |
| 2001/0000041 A1 | 3/2001 | Selmon et al. |
| 2001/0011162 A1 | 8/2001 | Epstein |
| 2002/0120180 A1 | 8/2002 | Speier et al. |
| 2002/0166946 A1 | 11/2002 | Iizuka et al. |
| 2004/0073088 A1 | 4/2004 | Friedman et al. |
| 2005/0025646 A1 | 2/2005 | Miller et al. |
| 2005/0085694 A1 | 4/2005 | Nakao |
| 2005/0171470 A1 | 8/2005 | Kucklick et al. |
| 2005/0197531 A1 | 9/2005 | Cabiri et al. |
| 2005/0267330 A1 | 12/2005 | Deppmeier et al. |
| 2006/0007427 A1 | 1/2006 | Sekiya et al. |
| 2006/0020165 A1 | 1/2006 | Adams |
| 2006/0041186 A1 | 2/2006 | Vancaillie |
| 2006/0069306 A1 | 3/2006 | Banik et al. |
| 2006/0074274 A1 | 4/2006 | Friedman et al. |
| 2006/0199998 A1 | 9/2006 | Akui et al. |
| 2006/0211916 A1 | 9/2006 | Kasahara et al. |
| 2006/0258906 A1 | 11/2006 | Binmoeller |
| 2006/0264995 A1 | 11/2006 | Fanton et al. |
| 2006/0276688 A1 | 12/2006 | Surti |
| 2007/0106113 A1 | 5/2007 | Ravo |
| 2007/0138206 A1 | 6/2007 | Yamamoto et al. |
| 2007/0213668 A1 | 9/2007 | Spitz |
| 2007/0270646 A1 | 11/2007 | Weiner |
| 2008/0021279 A1 | 1/2008 | Takahashi |
| 2008/0045859 A1 | 2/2008 | Fritsch et al. |
| 2008/0072970 A1 | 3/2008 | Gasser et al. |
| 2008/0081948 A1 | 4/2008 | Weisenburgh et al. |
| 2008/0091074 A1 | 4/2008 | Kumar et al. |
| 2008/0200764 A1 | 8/2008 | Okada |
| 2008/0242935 A1 | 10/2008 | Inoue |
| 2008/0255424 A1 | 10/2008 | Durgin et al. |
| 2008/0262308 A1 | 10/2008 | Prestezog et al. |
| 2009/0005643 A1 | 1/2009 | Smith et al. |
| 2009/0198105 A1 | 8/2009 | Sugisawa |
| 2009/0205189 A1 | 8/2009 | Nimkar et al. |
| 2009/0234193 A1 | 9/2009 | Weisenburgh, II et al. |
| 2009/0244223 A1 | 10/2009 | Mizutani et al. |
| 2010/0016786 A1 | 1/2010 | Modesitt et al. |
| 2010/0019786 A1 | 1/2010 | Potok et al. |
| 2010/0081878 A1 | 4/2010 | Byers et al. |
| 2010/0198012 A1 | 8/2010 | Poole et al. |
| 2010/0198014 A1 | 8/2010 | Poll et al. |
| 2011/0208001 A1 | 8/2011 | Haeckl et al. |
| 2011/0230716 A1 | 9/2011 | Fujimoto |
| 2011/0230717 A1 | 9/2011 | Konstorum et al. |
| 2011/0295066 A1 | 12/2011 | Fan |
| 2012/0065569 A1 | 3/2012 | Steegers et al. |
| 2012/0178995 A1 | 7/2012 | Newton, IV |
| 2012/0316394 A1 | 12/2012 | Yoshida et al. |
| 2013/0205936 A1 | 8/2013 | Schmieding et al. |
| 2013/0211433 A1 | 8/2013 | Kadykowski et al. |
| 2013/0217970 A1 | 8/2013 | Weisenburgh, II et al. |
| 2013/0267777 A1 | 10/2013 | Avitsian et al. |
| 2013/0289595 A1 | 10/2013 | Edwards et al. |
| 2014/0163360 A1 | 6/2014 | Stevens-Wright et al. |
| 2014/0364871 A1 | 12/2014 | Kucklick et al. |
| 2015/0045678 A1 | 2/2015 | Ohzawa et al. |
| 2015/0087906 A1 | 3/2015 | Kucklick et al. |
| 2015/0087907 A1 | 3/2015 | Konstorum et al. |
| 2015/0087908 A1 | 3/2015 | Cheng et al. |
| 2015/0087909 A1 | 3/2015 | Cheng et al. |
| 2015/0087911 A1 | 3/2015 | Konstorum et al. |
| 2015/0182108 A1 | 7/2015 | Fukuda |
| 2015/0257633 A1 | 9/2015 | Hassidov et al. |
| 2015/0282695 A1 | 10/2015 | Tay et al. |
| 2016/0089006 A1 | 3/2016 | Poll et al. |
| 2016/0095510 A1 | 4/2016 | Oskin et al. |
| 2016/0220100 A1 | 8/2016 | Cheng et al. |
| 2018/0192858 A1 | 7/2018 | Konstorum et al. |
| 2018/0353057 A1 | 12/2018 | Cheng et al. |
| 2020/0015665 A1 | 1/2020 | Konstorum et al. |

FOREIGN PATENT DOCUMENTS

| | | |
|---|---|---|
| CN | 102149312 A | 8/2011 |
| CN | 102348404 A | 2/2012 |
| CN | 102813496 A | 12/2012 |
| CN | 105491935 A | 4/2016 |
| CN | 105491938 A | 4/2016 |
| CN | 105491938 B | 11/2018 |
| CN | 105491935 B | 6/2019 |
| EP | 0374727 A1 | 6/1990 |
| EP | 1323381 A1 | 7/2003 |
| EP | 3016572 A1 | 5/2016 |
| EP | 3016574 A1 | 5/2016 |
| JP | 62-18101 U | 2/1987 |
| JP | H05/038323 A | 2/1993 |
| JP | H06/189893 A | 7/1994 |
| JP | H07275185 A | 10/1995 |
| JP | H07308286 A | 11/1995 |
| JP | H08501720 A | 2/1996 |
| JP | H08173370 A | 7/1996 |
| JP | H08243071 A | 9/1996 |
| JP | 2003167202 A | 6/2003 |
| JP | 2005/040184 A | 2/2005 |
| JP | 2007117289 A | 5/2007 |
| JP | 2008289850 A | 12/2008 |
| JP | 2009247797 A | 10/2009 |
| JP | 2012/045325 A | 3/2012 |
| JP | 2012523855 A | 10/2012 |
| JP | 2012254188 A | 12/2012 |
| JP | 2016529032 A | 9/2016 |
| JP | 2016529033 A | 9/2016 |
| JP | 6297156 B2 | 3/2018 |
| JP | 2018114296 A | 7/2018 |
| JP | 6526272 B2 | 5/2019 |
| JP | 2019166332 A | 10/2019 |
| WO | 2002/033296 A2 | 4/2002 |
| WO | 2012/069592 A1 | 5/2012 |
| WO | WO-2015047980 A1 | 4/2015 |
| WO | WO-2015047990 A1 | 4/2015 |
| WO | WO-2015048270 A1 | 4/2015 |
| WO | WO-2015048406 A1 | 4/2015 |

OTHER PUBLICATIONS

International Search Report, Application No. PCT/US2014/057659, dated Dec. 23, 2014.

Potentially Related Application, U.S. Appl. No. 14/493,581, dated Sep. 23, 2014.

Potentially Related Application, U.S. Appl. No. 14/496,473, dated Sep. 25, 2014.

Potentially Related Application, U.S. Appl. No. 14/493,700, dated Sep. 23, 2014.

Potentially Related Application, U.S. Appl. No. 14/551,208, dated Nov. 24, 2014.

Potentially Related Application, U.S. Appl. No. 14/551,440, dated Nov. 24, 2014.

"An Endoscope System Including a Resilient Reservoir", Potentially Related Application, U.S. Appl. No. 14/497,815, filed Sep. 26, 2014, 24 pgs.

"U.S. Appl. No. 14/493,700, 312 Amendment filed Aug. 21, 2018", 5 pgs.

"U.S. Appl. No. 14/493,700, Advisory Action dated Sep. 28, 2017", 3 pgs.

"U.S. Appl. No. 14/493,700, Advisory Action dated Nov. 17, 2016", 3 pgs.

"U.S. Appl. No. 14/493,700, Appeal Decision dated Jul. 11, 2018", 2 pgs.

"U.S. Appl. No. 14/493,700, Examiner Interview Summary dated May 11, 2017", 4 pgs.

"U.S. Appl. No. 14/493,700, Examiner Interview Summary dated May 24, 2018", 4 pgs.

(56) References Cited

OTHER PUBLICATIONS

"U.S. Appl. No. 14/493,700, Examiner Interview Summary dated Jun. 27, 2016", 4 pgs.
"U.S. Appl. No. 14/493,700, Final Office Action dated Mar. 21, 2018", 9 pgs.
"U.S. Appl. No. 14/493,700, Final Office Action dated Jun. 15, 2017", 8 pgs.
"U.S. Appl. No. 14/493,700, Final Office Action dated Sep. 7, 2016", 12 pgs.
"U.S. Appl. No. 14/493,700, Non Final Office Action dated Feb. 3, 2017", 10 pgs.
"U.S. Appl. No. 14/493,700, Non Final Office Action dated Mar. 23, 2016", 12 pgs.
"U.S. Appl. No. 14/493,700, Non Final Office Action dated Nov. 16, 2017", 10 pgs.
"U.S. Appl. No. 14/493,700, Notice of Allowance dated Jul. 23, 2018", 7 pgs.
"U.S. Appl. No. 14/493,700, Pre-Appeal Brief filed Jun. 12, 2018", 5 pgs.
"U.S. Appl. No. 14/493,700, PTO Response to Rule 312 Communication dated Sep. 6, 20", 2 pgs.
"U.S. Appl. No. 14/493,700, Response filed Feb. 15, 2018 to Non Final Office Action dated Nov. 16, 2017", 11 pgs.
"U.S. Appl. No. 14/493,700, Response filed May 3, 2017 to Non Final Office Action dated Feb. 3, 2017", 16 pgs.
"U.S. Appl. No. 14/493,700, Response filed Jun. 23, 2016 to Non Final Office Action dated Mar. 23, 2016", 16 pgs.
"U.S. Appl. No. 14/493,700, Response filed Aug. 15, 2017 to Final Office Action dated Jun. 15, 2017", 11 pgs.
"U.S. Appl. No. 14/493,700, Response filed Oct. 16, 2017 to Advisory Action dated Sep. 28, 2017", 16 pgs.
"U.S. Appl. No. 14/493,700, Response filed Nov. 7, 2016 to Final Office Action dated Sep. 7, 2016", 13 pgs.
"U.S. Appl. No. 14/496,473, 312 Amendment filed Jun. 12, 2018", 4 pgs.
"U.S. Appl. No. 14/496,473, Advisory Action dated Jul. 27, 2017", 3 pgs.
"U.S. Appl. No. 14/496,473, Advisory Action dated Dec. 7, 2016", 3 pgs.
"U.S. Appl. No. 14/496,473, Examiner Interview Summary May 3, 2017", 2 pgs.
"U.S. Appl. No. 14/496,473, Final Office Action dated May 11, 2017", 8 pgs.
"U.S. Appl. No. 14/496,473, Final Office Action dated Sep. 13, 2016", 7 pgs.
"U.S. Appl. No. 14/496,473, Final Office Action dated Dec. 29, 2017", 11 pgs.
"U.S. Appl. No. 14/496,473, Non Final Office Action dated Jan. 17, 2017", 9 pgs.
"U.S. Appl. No. 14/496,473, Non Final Office Action dated Apr. 22, 2016", 9 pgs.
"U.S. Appl. No. 14/496,473, Non Final Office Action dated Aug. 31, 2017", 7 pgs.
"U.S. Appl. No. 14/496,473, Notice of Allowance dated May 23, 2018", 8 pgs.
"U.S. Appl. No. 14/496,473, PTO Response to Rule 312 Communication dated Jun. 22, 2018", 2 pgs.
"U.S. Appl. No. 14/496,473, Response filed Feb. 15, 2018 to Final Office Action dated Dec. 29, 2017", 14 pgs.
"U.S. Appl. No. 14/496,473, Response filed Mar. 24, 2016 to Restriction Requirement dated Mar. 3, 2016", 6 pgs.
"U.S. Appl. No. 14/496,473, Response filed Apr. 17, 2017 to Non Final Office Action dated Jan. 17, 2017", 14 pgs.
"U.S. Appl. No. 14/496,473, Response filed Jul. 7, 2016 to Non Final Office Action dated Apr. 22, 2016", 12 pgs.
"U.S. Appl. No. 14/496,473, Response filed Jul. 11, 2017 to Final Office Action dated May 11, 2017", 13 pgs.
"U.S. Appl. No. 14/496,473, Response filed Nov. 14, 2016 to Final Office Action dated Sep. 13, 2016", 12 pgs.
"U.S. Appl. No. 14/496,473, Response filed Nov. 30, 2017 to Non Final Office Action dated Aug. 31, 2017", 13 pgs.
"U.S. Appl. No. 14/496,473, Restriction Requirement dated Mar. 3, 2016", 6 pgs.
"U.S. Appl. No. 14/497,815, 312 Amendment filed Mar. 28, 2016", 6 pgs.
"U.S. Appl. No. 14/497,815, Examiner Interview Summary dated Feb. 29, 2016", 3 pgs.
"U.S. Appl. No. 14/497,815, Non Final Office Action dated Dec. 21, 2015", 9 pgs.
"U.S. Appl. No. 14/497,815, Notice of Allowance dated Mar. 21, 2016", 9 pgs.
"U.S. Appl. No. 14/497,815, PTO Response to Rule 312 Communication dated Apr. 6, 2016", 2 pgs.
"U.S. Appl. No. 14/497,815, Response filed Feb. 25, 2016 to Non Final Office Action dated Dec. 21, 2015", 11 pgs.
"U.S. Appl. No. 14/497,815, Response filed Dec. 2, 2015 to Restriction Requirement dated Nov. 23, 2015", 4 pgs.
"U.S. Appl. No. 14/497,815, Restriction Requirement dated Nov. 23, 2015", 7 pgs.
"U.S. Appl. No. 15/095,651, 312 Amendment filed Jun. 8, 2018", 7 pgs.
"U.S. Appl. No. 15/095,651, Non Final Office Action dated Jan. 16, 2018", 9 pgs.
"U.S. Appl. No. 15/095,651, Notice of Allowance dated Mar. 30, 2018", 8 pgs.
"U.S. Appl. No. 15/095,651, Preliminary Amendment filed Apr. 11, 2016", 7 pgs.
"U.S. Appl. No. 15/095,651, PTO Response to 312 Communication dated Jun. 20, 2018", 2 pgs.
"U.S. Appl. No. 15/095,651, Response filed Feb. 21, 2018 to Non Final Office Action dated Jan. 16, 2018", 9 pgs.
"U.S. Appl. No. 15/095,651, Response filed Dec. 5, 2017 to Restriction Requirement dated Nov. 14, 2017", 7 pgs.
"U.S. Appl. No. 15/095,651, Restriction Requirement dated Nov. 14, 2017", 6 pgs.
"U.S. Appl. No. 15/917,212, 312 Amendment filed Sep. 24, 2019", 5 pgs.
"U.S. Appl. No. 15/917,212, Corrected Notice of Allowability dated Sep. 4, 2019", 4 pgs.
"U.S. Appl. No. 15/917,212, Examiner Interview Summary dated May 21, 2019", 3 pgs.
"U.S. Appl. No. 15/917,212, Non Final Office Action dated Mar. 26, 2019", 10 pgs.
"U.S. Appl. No. 15/917,212, Notice of Allowance dated Jul. 15, 2019", 7 pgs.
"U.S. Appl. No. 15/917,212, Notice of Non-Compliant Amendment dated Feb. 15, 2019", 3 pgs.
"U.S. Appl. No. 15/917,212, Preliminary Amendment filed Mar. 9, 2018", 6 pgs.
"U.S. Appl. No. 15/917,212, PTO Response to Rule 312 Communication dated Oct. 17, 2019", 2 pgs.
"U.S. Appl. No. 15/917,212, Response filed Jan. 22, 2019 to Restriction Requirement dated Nov. 27, 2018", 7 pgs.
"U.S. Appl. No. 15/917,212, Response filed Feb. 20, 2019 to Notice of Non-Compliant Amendment dated Feb. 15, 2019", 8 pgs.
"U.S. Appl. No. 15/917,212, Response filed May 22, 2019 to Non Final Office Action dated Mar. 26, 2019", 13 pgs.
"U.S. Appl. No. 15/917,212, Restriction Requirement dated Nov. 27, 2018", 6 pgs.
"U.S. Appl. No. 16/106,390, Non Final Office Action dated May 21, 2019", 15 pgs.
"U.S. Appl. No. 16/106,390, Notice of Allowance dated Dec. 17, 2019", 8 pgs.
"U.S. Appl. No. 16/106,390, Preliminary Amendment filed Aug. 21, 2018", 6 pgs.
"U.S. Appl. No. 16/106,390, Response filed Aug. 21, 2019 to Non Final Office Action dated May 21, 2019", 12 pgs.
"U.S. Appl. No. 16/580,079, Preliminary Amendment filed Sep. 24, 2019", 6 pgs.
"Chinese Application Serial No. 20140047065.X, Office Action dated Sep. 11, 2018", with English translation of claims, 12 pgs.

(56) References Cited

OTHER PUBLICATIONS

"Chinese Application Serial No. 201480047065.X, Office Action dated Feb. 28, 2017", with English translation of claims, 13 pgs.
"Chinese Application Serial No. 201480047065.X, Office Action dated Mar. 13, 2018", English translation, 8 pgs.
"Chinese Application Serial No. 201480047342.7, Office Action dated Mar. 27, 2017", with English translation of claims.
"Chinese Application Serial No. 201480047342.7, Office Action dated Dec. 14, 2017", with English translation of claims, 10 pgs.
"European Application Serial No. 14777479.8, Communication Pursuant to Article 94(3) EPC dated May 14, 2019", 6 pgs.
"European Application Serial No. 14777479.8, Communication Pursuant to Article 94(3) EPC dated Dec. 18, 2019", 4 pgs.
"European Application Serial No. 14777479.8, Response filed Sep. 6, 2019 to Communication Pursuant to Article 94(3) EPC dated May 14, 2019", 47 pgs.
"European Application Serial No. 14777479.8, Response to Communication pursuant to Rules 161(1) and 162 EPC dated Sep. 6, 2016", 9 pgs.
"European Application Serial No. 14781019.6, Communication Pursuant to Article 94(3) EPC dated Apr. 24, 2019", 7 pgs.
"European Application Serial No. 14781019.6, Communication Pursuant to Article 94(3) EPC dated Dec. 18, 2019", 6 pgs.
"European Application Serial No. 14781019.6, Response filed Aug. 23, 2019 to Communication Pursuant to Article 94(3) EPC dated Apr. 24, 2019", 2 pgs.
"European Application Serial No. 14781019.6, Response filed Sep. 7, 2016", 11 pgs.
"International Application Serial No. PCT/US2014/056911, International Preliminary Report on Patentability dated Apr. 7, 2016", 7 pgs.
"International Application Serial No. PCT/US2014/056911, International Search Report dated Dec. 12, 2014", 4 pgs.
"International Application Serial No. PCT/US2014/056911, Written Opinion dated Dec. 12, 2014", 5 pgs.
"International Application Serial No. PCT/US2014/057429, International Preliminary Report on Patentability dated Apr. 7, 2016", 10 pgs.
"International Application Serial No. PCT/US2014/057429, International Search Report dated Feb. 19, 2015", 5 pgs.
"International Application Serial No. PCT/US2014/057429, Written Opinion dated Feb. 19, 2015", 8 pgs.
"Japanese Application Serial No. 2016-537951, Amendment filed Feb. 26, 2016", W/ English Translation, 6 pgs.
"Japanese Application Serial No. 2016-537951, Decision in Trial to Reject mailed Oct. 23, 2019", w/ English Translation, 54 pgs.
"Japanese Application Serial No. 2016-537951, Decision of Rejection dated Aug. 28, 2018", W/ English Translation, 4 pgs.
"Japanese Application Serial No. 2016-537951, Notice of Reason for Rejection dated Jan. 31, 2017", W/ English Translation, 8 pgs.
"Japanese Application Serial No. 2016-537951, Notice of Reason for Rejection dated May 8, 2018", W/ English Translation, 8 pgs.
"Japanese Application Serial No. 2016-537951, Notice of Reason for Rejection dated Oct. 3, 2017", W/ English Translation, 9 pgs.
"Japanese Application Serial No. 2016-537951, Response filed Apr. 28, 2017 to Notice of Reason for Rejection dated Jan. 31, 2017", W/ English Translation, 19 pgs.
"Japanese Application Serial No. 2016-537951, Response filed Jul. 31, 2018 to Notice of Reason for Rejection dated May 8, 2018", with English translation of claims, 13 pgs.
"Japanese Application Serial No. 2016-537951, Response filed Dec. 5, 2018 to Decision of Rejection dated Aug. 28, 2018", with English translation of claims, 4 pgs.
"Japanese Application Serial No. 2016-537951, Response filed Dec. 28, 2017 to Notice of Reason for Rejection dated Oct. 3, 2017", with English Translation, 12 pgs.
"Japanese Application Serial No. 2016-537952, Decision to Grant dated Jan. 23, 2018", English translation, 2 pgs.
"Japanese Application Serial No. 2016-537952, Notice of Reasons for Rejection dated Jan. 31, 2017", with English translation of claims, 12 pgs.
"Japanese Application Serial No. 2016-537952, Office Action dated Oct. 3, 2017", with English translation of claims, 4 pgs.
"Japanese Application Serial No. 2016-537952, Response filed May 8, 2017 to Written Opinion dated Apr. 28, 2019", with English translation of claims, 24 pgs.
"Japanese Application Serial No. 2016-537952, Response filed Dec. 21, 2017 to Notice of Reasons for Refusal dated Sep. 27, 2017", with English translation of claims, 11 pgs.
"Japanese Application Serial No. 2016-537952, Written Opinion dated Apr. 28, 2017", with English translation of claims, 19 pgs.
"Japanese Application Serial No. 2016-537952, Written Statement filed May 2, 2017", with English translation of claims, 7 pgs.
"Japanese Application Serial No. 2018-028128, Notice of Reasons for Refusal dated Dec. 18, 2018", with English translation of claims, 6 pgs.
"Japanese Application Serial No. 2018-028128, Written Amendment filed Feb. 20, 2018", with English translation of claims, 4 pgs.
"Japanese Application Serial No. 2018-028128, Written Amendment filed Mar. 14, 2019", with English translation of claims, 2 pgs.
"Japanese Application Serial No. 2019-0878875, Written Amendment filed Jun. 5, 2019", with English translation of claims, 3 pgs.
"U.S. Appl. No. 14/493,581, Advisory Action dated Jan. 12, 2018", 3 pgs.
"U.S. Appl. No. 14/493,581, Advisory Action dated Apr. 26, 2017", 3 pgs.
"U.S. Appl. No. 14/493,581, Advisory Action dated Aug. 19, 2016", 3 pgs.
"U.S. Appl. No. 14/493,581, Applicant's Summary of Examiner Interview filed Sep. 26, 2016", 1 pg.
"U.S. Appl. No. 14/493,561, Examiner Interview Summary dated Apr. 18, 2016", 3 pgs.
"U.S. Appl. No. 14/493,581, Examiner interview Summary dated Aug. 24, 2016", 3 pgs.
"U.S. Appl. No. 14/493,581, Final Office Action dated Feb. 9, 2017", 11 pgs.
"U.S. Appl. No. 14/493,581, Final Office Action dated May 18, 2016", 10 pgs.
"U.S. Appl. No. 14/493,581, Final Office Action dated Oct. 19, 2017", 11 pgs.
"U.S. Appl. No. 14/493,581, Non Final Office Action dated Jan. 29, 2016", 13 pgs.
"U.S. Appl. No. 14/493,581, Non Final Office Action dated Jun. 29, 2017", 10 pgs.
"U.S. Appl. No. 14/493,581, Non Final Office Action dated Oct. 5, 2016", 9 pgs.
"U.S. Appl. No. 14/493,581, Response filed Apr. 3, 2017 to Final Office Action dated Feb. 9, 2017", 14 pgs.
"U.S. Appl. No. 14/493,581, Response filed Apr. 21, 2016 to Non Final Office Action dated Jan. 29, 2016", 14 pgs.
"U.S. Appl. No. 14/493,581, Response filed Jul. 13, 2016 to Final Office Action dated May 18, 2016", 10 pgs.
"U.S. Appl. No. 14/493,581, Response filed Sep. 13, 2017 to Non Final Office Action dated Jun. 29, 2017", 14 pgs.
"U.S. Appl. No. 14/493,581, Response filed Dec. 18, 2017 to Final Office Action dated Oct. 19, 2017", 15 pgs.
"U.S. Appl. No. 14/493,581, Response filed Dec. 29, 2016 to Non Final Office Action dated Oct. 5, 2016", 13 pgs.
"U.S. Appl. No. 16/106,390, Corrected Notice of Allowability dated Feb. 24, 2020", 4 pgs.
"U.S. Appl. No. 16/106,390, Corrected Notice of Allowability dated Mar. 12, 2020", 5 pgs.
"Chinese Application Serial No. 201480047065.X, Office Action dated Sep. 11, 2018", w/ English Translation, 13 pgs.
"Chinese Application Serial No. 201480047065.X, Response filed Feb. 21, 2019 to Office Action dated Sep. 11, 2018", with machine translation, 14 pgs.
"Chinese Application Serial No. 201480047065.X, Response filed May 25, 2018 to Office Action dated Mar. 13, 2018", with machine translation, 19 pgs.

(56) References Cited

OTHER PUBLICATIONS

"Chinese Application Serial No. 201480047065.X, Response filed Nov. 23, 2018 to Office Action dated Sep. 11, 2018", with machine translation, 19 pgs.

"Chinese Application Serial No. 201480047342.7, Office Action dated May 31, 2018", w/ English Translation, 12 pgs.

"Chinese Application Serial No. 201480047342.7, Response filed Jan. 22, 2018 to Office Action dated Dec. 14, 2017", with machine translation, 19 pgs.

"Chinese Application Serial No. 201480047342.7, Response filed Aug. 3, 2017 to Office Action dated Mar. 27, 2017", with machine translation, 19 pgs.

"Chinese Application Serial No. 201480047342.7, Response filed Aug. 14, 2018 to Office Action dated May 31, 2018", with machine translation, 17 pgs.

"Chinese Application Serial No. 201480047342.7, Response filed Sep. 14, 2018 to Office Action dated May 31, 2018", with machine translation, 14 pgs.

"European Application Serial No. 14777479.8,. Response filed Apr. 16, 2020 to Office Action dated Dec. 18, 2019", 6 pgs.

"European Application Serial No. 14781019.6, Response filed Apr. 11, 2020 to Communication Pursuant to Article 94(3) EPC dated Dec. 18, 2019", 70 pgs.

"International Application Serial No. PCT/US2014/056890, International Preliminary Report on Patentability dated Apr. 7, 2016", 8 pgs.

"International Application Serial No. PCT/US2014/056890, International Search Report dated Feb. 4, 2015", 5 pgs.

"International Application Serial No. PCT/US2014/056890, Written Opinion dated Feb. 4, 2015", 6 pgs.

"International Application Serial No. PCT/US2014/057659, International Preliminary Report on Patentability dated Apr. 7, 2016", 8 pgs.

"International Application Serial No. PCT/US2014/057659, Written Opinion dated Dec. 23, 2014", 6 pgs.

Cheng, Ming, et al., "Adjustable Endoscope Sheath", Potentially Related U.S. Appl. No. 14/551,440, filed Nov. 24, 2014, 25 pgs.

"European Application Serial No. 14777479.5, Communication Pursuant to Article 94(3) EPC dated Jun. 12, 2020", 4 pgs.

"Japanese Application Serial No. 2019-087875, Notification of Reasons for Rejection dated Jun. 16, 2020", w/ English Translation, 12 pgs.

\* cited by examiner

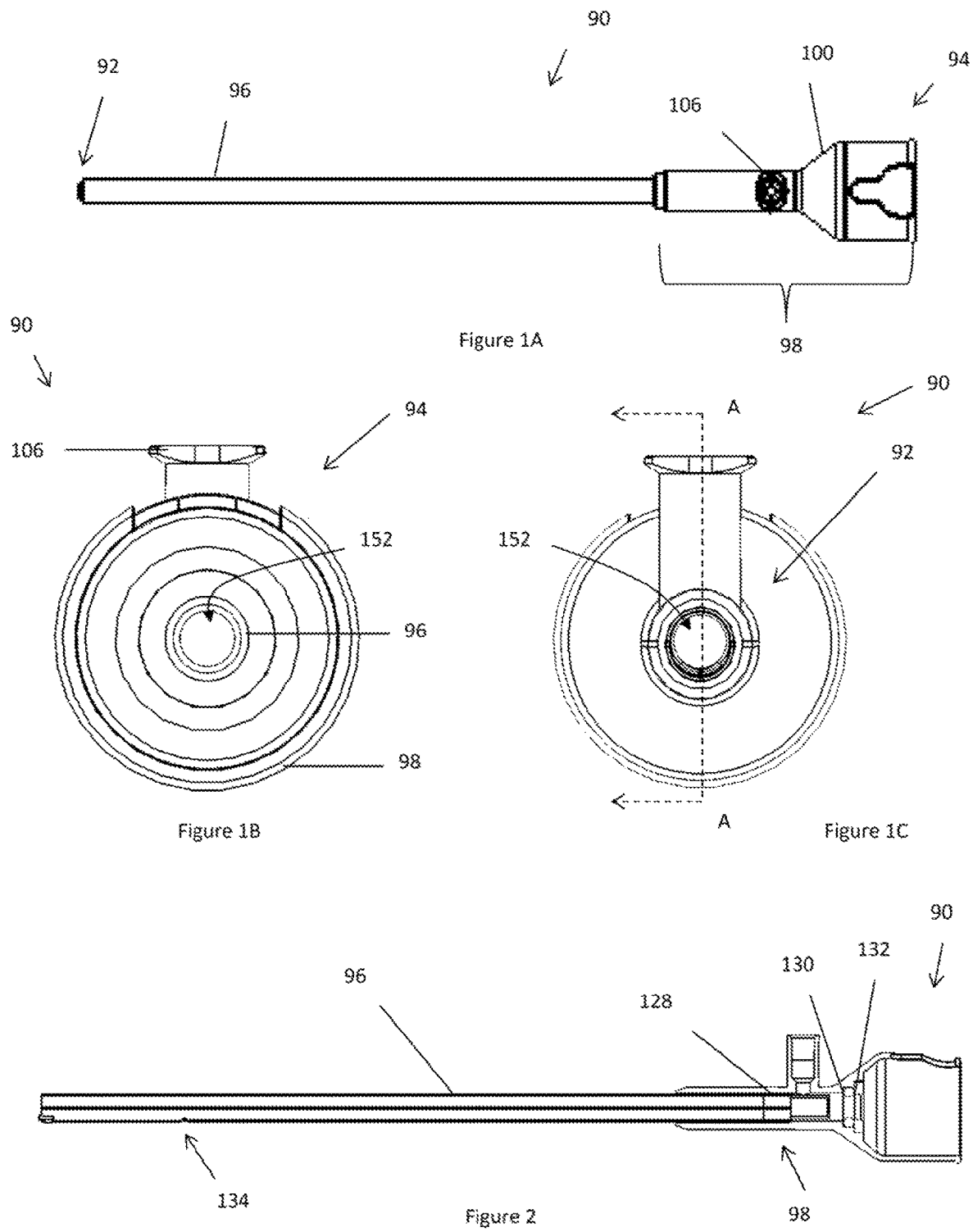

ENDOSCOPE SYSTEM INCLUDING A RESILIENT RESERVOIR

FIELD

The present teachings generally relate to a system including endoscope sheath that assists in washing a lens and/or imaging device of an endoscope and resilient reservoir for supplying irrigation fluid.

BACKGROUND

Endoscopes are typically used for minimally invasive surgery or to provide access to an internal location of a patient so that a doctor is provided with visual access. Endoscopes, during use, may be inserted into a location that may include debris that may cover the end of the endoscope and especially cover an imaging device located at the end of the endoscope. For example, an endoscope being used for surgery may become covered by blood and the blood may impair the vision of a surgeon so that surgery becomes increasingly difficult. Attempts have been made to provide various devices and systems to assist a surgeon in clearing debris from the imaging device of the endoscope and restore vision. These devices may remove some of the debris from the imaging device of the endoscope, however, these devices may not remove all of the debris and/or may leave spots or droplets on the imaging device, which may result in continued impairment. These devices may have features that attempt to control the flow of fluid, suction, or both at the end of the endoscope in an attempt to clear debris, spots, droplets, or a combination thereof from the endoscope. Further, some of the endoscope systems leave droplets on the imaging device and/or lens and these droplets may inhibit vision through the lens and/or imaging device. Additionally, irrigation fluid and suction may be controlled by pressing one or more buttons located on the endoscope sheath which may result in repositioning of the endoscope during washing and/or cleaning or may cause the surgeon to reposition the endoscope within their hand.

Examples of some endoscope cleaning systems and actuation devices to control the endoscope cleaning systems may be found in U.S. Pat. Nos. 5,505,707; 5,575,756; 5,630,795; 6,447,446; 8,079,952; 8,231,574 and U.S. Patent Application Publication Nos. 2005/0025646, 2008/0081948, and 2013/0289595 all of which are incorporated by reference herein in their entirety herein for all purposes. It would be attractive to have an endoscope system that washes an endoscope lens and/or imaging device and removes all debris and fluid droplets so that vision is not impaired. What is needed is a method of cleaning where there is no delay between an irrigation step and a suction step. What is needed is method of cleaning the endoscope where the irrigation step and suction step are triggered by a single action. It would be attractive to have an endoscope system that is free of a pump and is controlled by a foot system.

SUMMARY

The present teachings meet one or more of the present needs by providing: a system comprising: (a) a sheath configured to receive all or a portion of an endoscope; (b) an irrigation line connecting the sheath to an irrigation source; (c) a suction line connecting the sheath to a suction source; and (d) a control module located between the sheath, and the irrigation source and the suction source and controls flow of irrigation fluid from the irrigation source to the sheath and movement of suction between the suction source and the sheath; wherein the irrigation source is connected to a resilient reservoir that is located within the control module and movement of the control module compresses the resilient reservoir moving irrigation fluid from the resilient reservoir to the sheath so that the irrigation fluid assists in cleaning the endoscope, and wherein the control module includes a valve and compression of the resilient reservoir initiates movement of the valve so that the valve opens and suction from the suction line is applied to the sheath.

Another possible embodiment of the present teachings comprises: a method comprising: (a) connecting a sheath to an endoscope; (b) connecting a delivery line to the sheath; (c) connecting a suction source to a control module by a suction line; (d) connecting an irrigation source to the control module by an irrigation line; and (e) connecting the control module to the delivery line by the suction line and the irrigation line so that suction and irrigation fluid extend through the control module; wherein application of the irrigation fluid and application of the suction are provided from a single event.

The teachings herein provide an endoscope system that washes an endoscope lens and/or imaging device and removes all debris and fluid droplets so that vision is not impaired. The teachings herein provide a method of cleaning where there is no delay between an irrigation step and a suction step. The teachings herein provide a method of cleaning the endoscope where the irrigation step and suction step are triggered by a single action. The teachings herein provide an endoscope system that is free of a pump and is controlled by a foot system.

BRIEF DESCRIPTION OF THE DRAWINGS

FIG. 1A illustrates a top view of an endoscope sheath;

FIG. 1B illustrates a proximal end view of an endoscope sheath of FIG. 1A;

FIG. 1C illustrates a distal end view of an endoscope sheath of FIG. 1A;

FIG. 2 illustrates a cross sectional view of FIG. 1C along lines A-A;

DETAILED DESCRIPTION

Figure 3:
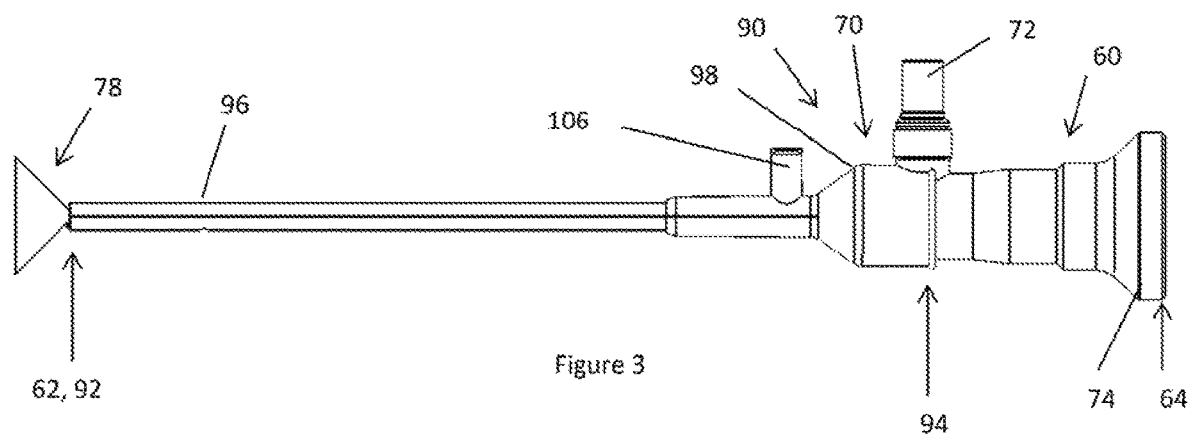
FIG. 3 illustrates a side view of an endoscope inserted in the endoscope sheath of FIG. 1A.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 61/882,652, filed on Sep. 26, 2013, the contents of which are incorporated by reference herein in their entirety for all reasons. The present teachings provide an endoscope sheath for use in a system. The system of the teachings herein includes an irrigation source and a suction source that are both connected to an endoscope sheath and are in communication with an endoscope. The system may include one or more control modules. The system may function to clean an endoscope. Preferably, the system functions to clean a distal end (i.e., a tip) of an endoscope. More preferably, the system functions to clean an imaging device of an endoscope. The system may include one or more functional components that may extend proximate to a distal end of an endoscope or beyond a distal end of an endoscope. The system may provide one or more conduits relative to the endoscope. The system may protect the endoscope. The system may include one or more sources of irrigation fluid for use with the system, and the one or more sources of irrigation fluid, suction, or both may be controlled by one or more control modules.

The one or more control modules may function to control the amount of fluid, suction, or both applied to a predetermined area, an area of interest, the endoscope, or a combination thereof. The one or more control modules may control the order of application of fluid, suction, or both relative to each other. The one or more control modules may function to stop suction, stop irrigation fluid, apply irrigation fluid, apply suction, or a combination of both. The one or more control modules may be powered by electricity, batteries, or both. The one or more control modules may include one or more pumps, one or more valves, one or more user interfaces, or a combination thereof. The one or more user interfaces may be one or more control knobs, one or more selectors, one or more top plates, one or more actuation petals, one or more poppet valves, one or more indicators, one or more user controls, one or more devices for changing a parameter, or a combination thereof. The one or more control modules may include any of the pumps discussed herein and based upon feedback from the user interface may control the pump to perform the selected parameter. The one or more control modules may control one or more valves. The one or more control modules may prevent application of suction and irrigation fluid at the same time. The one or more control modules may control one or more valves so that suction, irrigation fluid, or both may be applied in series, in parallel, simultaneously, one at a time, or a combination thereof. The one or more control modules may be physically connected, electrically connected, or both to one or more suction lines, one or more irrigation lines, one or more valves, or a combination thereof. The one or more control modules may control suction and irrigation fluid relative to each other. The control module may include a microprocessor, a computer, a control algorithm, or a combination thereof.

The control module may include one or more switches. The one or more switches of the control module may be in communication with one or more actuation members, one or more resilient reservoirs, or both. The one or more switches may be actuated by the resilient reservoir when the resilient reservoir is compressed. The one or more switches may be a pressure sensor. The one or more switches may be a flow sensor (e.g., that senses flow out of the resilient reservoir). The switch may be a magnetic switch (e.g., having two magnets that are moved into contact and/or apart from each other). For example, when the actuation member is compressed, two magnets may be moved together causing one or more events to occur and when the magnets are moved apart another event (or no event) may occur. The one or more switches may generate a signal, may be an event that sets off a series of events, or both. The control module may control one more valves located within the system, connected to the control module, or both. The one or more control modules may perform a suction function, an irrigation function, or a combination of both upon a selection by the user as is indicated by the user interface. The control module may control the running speed, pumping duration, suction duration, or a combination thereof of the pump so that irrigation fluid is moved to the sheath. The one or more control modules may be part of a stand, part of a foot petal, or a combination of both.

The one or more control modules may be located at an elevated position so that a user may adjust the control module, activate the control module, or both using hand controls (e.g., a console). The one or more control modules may be located on a floor position so that the user may adjust the control module using one or both feet. The one or more control modules may be part of a foot switch, a foot activation device, a foot petal, or a combination thereof. Functionality of the control module may be separated between a foot petal (e.g., a foot console) and an elevated portion of the control module (e.g., a hand console) and one or both may be used to control an actuation cycle. The foot control module may include one or more switches, one or more valves, one or more actuation devices, or a combination thereof. The suction lines, the irrigation lines, or both may be directly connected to the foot control module, the hand control module, or split between the two. Preferably, when a foot control module is used all of the functionality is located in the foot control module. The foot control module, the hand console, the control modules, or a combination thereof may include one or more actuation members.

The one or more actuation members may function to initiate an application of suction, irrigation fluid, or both. The one or more actuation members may function to initiate the application of suction and irrigation fluid with a single movement. The one or more actuation members may move relate to one or more parts of the control module. The one or more actuation members may move relative to a base of the control module. The one or more actuation members may pivot about a pivot point. The one or more actuation members may compress a resilient reservoir so that irrigation fluid is applied. The one or more actuation members may trigger an application of suction. The one or more actuation members may be electrically connected, mechanically connected, or both to one or more valves. The one or more actuation members may control a pressure of the irrigation fluid. For example, applying more pressure to the actuation member may result in the irrigation fluid being applied with more pressure. The amount of pressure applied to the actuation member may not affect the pressure of the irrigation fluid. The one or more actuation members may extend over one or more resilient reservoirs. The actuation member may be a finger switch, a foot pedal (or switch), or both. The actuation member may be part of a control module. The one or more actuation members may be connection to one or more base members.

The one or more base members (i.e., base) may function to support the control module. The one or more base members may function to support a resilient reservoir, one or more actuation members, or both. The one or more base members may be connected to one or more valves (e.g., check valves). The one or more base members may receive one or more lines (e.g., irrigation lines, suction lines, or both). The one or more base members may support the control module on a surface. The one or more base members may include mechanical controls, electrical controls, or both. The one or more base members may provide a pivot point so that the actuation member may move relative to the base member. The base member may create a pivot point for the actuation member to rotate about. A pin may extend through the actuation member connecting the actuation member to a base so that the actuation member may be rotated about the pin to create pressure on a resilient reservoir. The base member may support one or more resilient reservoirs so that the actuation member may move and compress the resilient reservoir to apply irrigation fluid.

The one or more resilient reservoirs may function to apply irrigation fluid. The one or more resilient reservoirs may function to generate pressure in applying irrigation fluid. The one or more resilient reservoirs may function to act as an intermediary point for irrigation fluid. The one or more resilient reservoirs may be connected to an irrigation source. The one or more resilient reservoirs may include an entrance port, an exit port, or both. The entrance port and the exit port may be the same port. For example, fluid may be moved into the resilient reservoir through an entrance port during filling and then exit the entrance port (i.e., exit port) during compression so that the fluid exits the resilient reservoir and is directed towards the sheath. The entrance port and the exit port may be located on opposite sides of the resilient reservoir. The entrance port and the exit port may include one or more valves and preferably one or more one way valves (i.e., check valves). The one or more resilient reservoirs may be a storage location for fluid. The one or more resilient reservoirs may be a temporary storage location for irrigation fluid. The one or more resilient reservoirs may hold a single application of irrigation fluid. The one or more resilient reservoirs may expand when filling and/or receiving irrigation fluid. The one or more resilient reservoirs may contract when expelling fluid, being compressed, or both. The one or more resilient reservoirs may have a volume that large enough to provide 1 or more, 2 or more, 3 or more, 4 or more, or even 5 or more applications of irrigation fluid. The one or more resilient reservoirs may have a volume to apply 10 or less, 8 or less, or 6 or less applications of irrigation fluid. The resilient reservoir may be a bulb. The resilient reservoir may return an actuation member back to a starting position, a steady state, an original position, or a combination thereof. The resilient reservoir may expand and draw irrigation fluid from an irrigation source. The resilient reservoir may generate a vacuum so that irrigation fluid is drawn from an irrigation source. The one or more resilient reservoirs may be made of any material that expands and contracts. The one or more resilient reservoirs may be made of a material that elastically deforms. The one or more resilient reservoirs may be made of a material that does not plastically deform. The one or more resilient reservoirs may be made of and/or include an elastomer, elastic, rubber, or a combination thereof. The one or more resilient reservoirs may be made of plastic. The one or more resilient reservoirs may be made of the same material as the one or more irrigation lines, one or more suction lines, one or more delivery lines, one or more common lines, or a combination thereof. The one or more resilient reservoirs may be made of a material that is capable of holding material a fluid without leaking. The irrigation fluid may function to clean an endoscope, clear debris from a location proximate to the endoscope, be bioabsorbable, or a combination thereof. The irrigation fluid may function to move solid particles, move opaque fluids, or both. The irrigation fluid may be applied with a pressure. The pressure of the irrigation fluid may be varied by changing the height of the irrigation source relative to the sheath so that the head of the irrigation fluid is increased or decreased. The pressure of the irrigation fluid may be sufficiently high so that the irrigation fluid may be redirected by a flow director. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about 1 MPa or less, or even about 0.75 MPa or less. The pressure of the irrigation fluid may be varied from application to application, during a single application, or both. For example, pressure of the irrigation fluid may be varied by varying the amount of pressure on the actuation member, the resilient reservoir, or both. The irrigation fluid may be applied with a sufficient amount of pressure that the surface tension of the irrigation fluid wicks the irrigation fluid across the distal end, the imaging portion, or both of the endoscope (e.g., the pressure may be low enough that the irrigation fluid remains in contact with the endoscope, the sheath, or both). The irrigation fluid may be stored in a location and the location may be an irrigation source. The irrigation source may store a sterile fluid. The irrigation source may be connected to a resilient reservoir by one or more supply lines. The irrigation source may be connected to a control module by a supply line so that the supply line supplies irrigation fluid directly and/or indirectly to a sheath. The irrigation source may provide irrigation fluid to a distal location via one or more supply lines. The irrigation fluid may be applied with a gravity feed, thus, the pressure of the irrigation fluid may be determined by the height of an irrigation source. For example, the irrigation source may be an IV bag and the height of the IV bag may determine the amount of pressure and/or force generated at the distal tip of the sheath, endoscope, or both. Preferably, the irrigation fluid is gravity fed from an irrigation source to a resilient reservoir and the resilient reservoir assists in generating pressure. The irrigation fluid may be applied by a pump that pumps the fluid at a predetermined pressure. Preferably, the irrigation fluid is not applied by a pump. The irrigation fluid may be continuously applied, intermittently applied, or both during an application cycle. The pressure of the irrigation fluid may change when the irrigation fluid reaches the end of an endoscope sheath so that the fluid cleans the endoscope, creates turbulence at the end of the endoscope, or both. Preferably, the pressure is sufficiently low so that the flow across the endoscope is laminar. The pressure of the irrigation fluid may be varied based upon the size, length, or both of an irrigation line extending between an irrigation source and the sheath. The irrigation source may be a reservoir that fluid is drawn from by a fluid movement mechanism (e.g., a pump and/or resilient reservoir) and moved through the sheath to provide irrigation to a distal end of an endoscope, to clean an endoscope, or both.

The pump may function to circulate irrigation fluid, move irrigation fluid through one or more lines, move fluid through a sheath, move irrigation fluid to a resilient reservoir, or a combination thereof. The pump may function to create a negative pressure (e.g., suction or vacuum). The pump may move fluid with an impeller. The pump may be a lobe pump, a centrifugal pump, a positive displacement pump, a rotary positive displacement pump, a diaphragm pump, peristaltic pump, rope pump, a gear pump, a screw pump, a progressing cavity pump, a roots-type pump, a plunger pump, or a combination thereof. Preferably, the pump moves a constant amount of fluid upon being activated, a constant amount of fluid may be varied from application to application, or both. More preferably, the pump is a peristaltic pump. Even more preferably, the system may be free of a pump to supply irrigation fluid through the irrigation lines.

The one or more irrigation lines may function to connect the sheath to an irrigation source, a resilient reservoir, one or more valves, or a combination thereof. The irrigation lines may function to create a head so that pressure is created and the irrigation fluid is applied with a force. The one or more irrigation lines may connect one or more resilient reservoirs with an irrigation source. The one or more irrigation lines may extend through a control module. The irrigation line may be flexible, movable, or both. The irrigation lines may be compressible. One or more and preferably a plurality of irrigation lines may extend between an irrigation source, a resilient reservoir, a control module, and the sheath. The one or more irrigation lines may connect to one or more entrance ports, one or more exit ports, or both of a sheath, a resilient reservoir, an irrigation source, or both. The irrigation lines may be made of any material that is compatible with the irrigation fluid, a patient, use in a surgical procedure, or a combination thereof. The irrigation lines may connect the sheath to an irrigation source, a suction source, or both (i.e., suction may be applied through the irrigation line).

The suction source may function to remove fluid, debris, opaque fluids, unwanted material, or a combination thereof from a point of interest, from a distal end of the sheath, a distal end of the endoscope, or a combination thereof. The suction source may function to perform a drying function, remove fluid spots, or both. The suction source may be a pump, reversal of a motor, a common suction source, a hospital suction source, or a combination thereof. The suction source may apply a sufficient amount of vacuum to remove a predetermined amount of fluid in a predetermined amount of time. For example, the suction source may apply suction so that 10 ml of fluid may be removed in 1 to 2 seconds. The suction source may apply suction for a predetermined amount of time. The predetermined amount of time may be about 2, 3, 4, 5, 6, 7, 8, 9, 10, 15, or 20 second or more. The suction source may continuously provide suction and one or more valves may open and close to control the application of the suction. The suction source may provide suction immediately after the irrigation source ceases to provide irrigation fluid, after a delay, or both. The suction source may apply a continuous suction, intermittent suction, or both.

The suction line may function to connect the sheath to the suction source so that suction may be pulled through the sheath. The suction line may function to connect the sheath to a suction source. The suction line may assist is moving fluids, removing fluids, removing debris, removing opaque fluids, removing particles, or a combination thereof. The suction line may be any line that may assist in creating a vacuum at a distal tip of the endoscope, the sheath, or both. The suction line and the irrigation line may be the same line. The suction line and the irrigation line may be connected to a common line. The suction line and the irrigation line may be connected by one or more fittings, one or more valves, or both.

The one or more valves may function to allow only one functions (e.g., irrigation or suction) to work at a time. The one or more valves may function to block the irrigation line, the suction line, or both. The one or more valves may only allow suction or irrigation to be applied at a given time. The one or more valves may be or include a check valve, a back flow preventer, or both. The one or more valves may be a poppet valve. The poppet valve may be any poppet valve taught herein including a poppet valve taught in U.S. Ser. No. 13/457,007 filed on Apr. 26, 2012 the teachings of which are incorporated by reference herein and specifically the teaching as to FIGS. 5-7. The one or more valves may be a two way valve, a valve that only allows for the application of a fluid and/or suction at one time. The one or more valves may be located proximate to the sheath, proximate to the irrigation source, proximate to the suction source, proximate to the resilient reservoir, or a location therebetween. Preferably each side of the resilient reservoir includes a valve. More preferably, each side of the resilient reservoir includes a check valve so that during an application of pressure fluid is prevented from being moved towards the irrigation source and during expansion of the resilient member, refiling of the resilient member, or both the resilient member does not create suction from the sheath. Each of the lines may include a valve. If more than one valve is present the valves may be electrically connected, hydraulically connected, fluidly connected, or a combination thereof so that if one valve is opened another valve is closed, a series of valves are opened, a series of valves are closed, or a combination thereof. The one or more valves may be mechanically controlled, electrically controlled, passive, active, or a combination thereof. The two or more valves (e.g., a first valve and a second valve) may be electrically connected, electrically controlled, or both. The two or more valves may be operated in a sequence (e.g., one opened and then one dosed), operated simultaneously, operated on a delay, or a combination thereof. For example, only one valve may be open at a time. In another example, one may close and after a time delay another may open. The one or more valves may be part of a common fitting, located proximate to a common fitting, or both.

The one or more common fittings may function to connect two or more lines into a common line. The one or more common fittings may function to connect a suction line and an irrigation line to a common port, a sheath, or both. The one or more common fittings may connect a single line to multiple devices so that multiple devices may be used simultaneously, in series, in parallel, or a combination thereof. For example, the common fitting may connect a suction line and an irrigation line to a common line that is connected to a sheath and, during operation, an irrigation fluid may be applied and then after a delay and/or immediately when the irrigation fluid ceases to be applied, suction may be applied to the suction line so that irrigation fluid, excess irrigation fluid, debris, particles, opaque fluids, or a combination thereof are removed from the distal end of the endoscope. The one or more common fittings may have two or more openings, three or more openings, four or more openings, or even five or more openings. Each opening may receive at least one line and fluidly connect the one or more lines together. More than one common fitting may be used to connect multiple lines together. For example, a first common fitting with three openings may be connected to second common fitting with three openings so that two tubes are connected to one opening of the first common fitting and one tube is connected to each of the other two openings. Preferably, the common fitting is generally "Y" shaped and two of the openings lead into a third opening that is connected to a common line and/or a delivery line.

The common line may function to deliver irrigation fluid, suction, or both to a sheath. The common line may function to provide a combination of multiple different fluids, devices, suction levels, fluid pressures, or a combination thereof. The common line may provide a single access point between the irrigation source and the suction source and the sheath. The common line may have an increased cross-sectional area (e.g., diameter) relative to the cross-sectional area of the irrigation line, the suction line, or both. The common line may be the same size (e.g., cross-section) as one or both of the irrigation line, the suction line, or both. The common line has a volume. The volume of the common line may be sufficiently large so that during application of suction the irrigation fluid is not entirely removed from the common line. For example, the common line may be entirely filled during a cycle of applying irrigation fluid and during the application of suction a portion of the common line may include air, be a mixed phase, or both. The common line may be sufficiently small so that during application of suction the line is completely evacuated. The common line may have a length of about 5 cm or more, 10 cm or more, 20 cm or more, or even about 50 cm or more. The common line may have a length of about 4 cm or less, about 3 cm or less, or about 2 cm or less. The common line may have a volume of about 5 ml or more, about 10 ml or more, about 15 ml or more, or even about 20 ml or more. The common line may have a volume of about 4 ml or less, about 3 ml or less, or even about 2 ml or less. The common line may be the same size as one or both of the irrigation lines and/or the suction lines. The common line may extend between the common fitting and a port of the sheath. The common line may be a delivery line.

The delivery line may function to deliver fluids to a sheath. The delivery line may function to deliver suction to the sheath. The delivery line and the common line are preferably the same line. The teachings herein for the common line are incorporated by reference here for the delivery line. The delivery line, common line, or both may be used during an application cycle.

The application cycle may be any cycle where an endoscope is cleaned. The application cycle may be a method of cleaning, washing, or both an endoscope. The application cycle may be a cycle where a combination of different items are applied, a combination of different sequences are performed, or both. The application cycle may be a cycle where an irrigation fluid and suction are applied in a sequence to clean an endoscope. The application cycle may be a combination of one or more applications of fluid, one or more applications of suction, or both. The application cycle may be an application of fluid and immediately thereafter an application of suction to remove excess fluid form a point of interest, the distal end of the endoscope, the distal end of the sheath, or a combination thereof. The application cycle may be triggered by a single event. For example, pressing an actuation member may trigger the application of irrigation fluid and a subsequent application of suction. The application cycle may be triggered by actuating the actuation member only. For example, upon pressing the actuation member a predetermined amount of fluid may be applied and then after a predetermined amount of time a predetermined amount of suction may be applied. A sequence of events resulting in the cleaning of the endoscope may be triggered from a single event (e.g., applying fluid, suction, refilling a resilient reservoir, opening and closing of valves, or a combination thereof). The application cycle may have no delay between an end of the application of an irrigation fluid and the beginning of the application of suction. For example, upon completion of the irrigation fluid being applied the suction may immediately begin. A delay may be present between an application of suction and an application of irrigation fluid. The delay may be for a predetermined amount of time. The delay may be for about 1 second or more, about 2 seconds or more, about 3 seconds or more, or about 4 seconds or more. The delay may be for about 10 seconds or less, about 8 seconds or less, or about 5 seconds or less. The application cycle may be varied by a user.

The application cycle may include only an application of fluid (i.e., a flushing cycle, a washing cycle) with no suction. The application cycle may be user activated for a predetermined amount of time. The application cycle may be activated based upon a duration a user activates a switch. For example, a user may pre-set the activation cycle so that one touch of the switch causes the irrigation fluid to run for 5 seconds. The user may pre-set the activation cycle so that no suction is used. The application cycle may be a concurrent application of fluid and suction. For example, suction may begin being applied before the irrigation fluid is turned off. The application cycle of the irrigation fluid, the suction, or both may be changed by a user changing a selector, actuating a control longer, changing an input, adjusting a control module, adjusting selector switches, adjusting a user interface, or a combination thereof. The application cycle may be sufficiently long so that an image sensor of an endoscope is clear and good images may be taken.

The endoscope may function to provide an image to a surgeon, a doctor, a nurse, any other person who desires visual access to a remote location, or a combination thereof. The endoscope may be used for non-invasive surgery. The endoscope may be used for orthoscopic surgery. The endoscope may be inserted in a cut in tissue. The endoscope may be used for insertion into an orifice including an ear, nose, throat, rectum, urethra, or a combination thereof. The endoscope may have a generally circular cross-section. The endoscope may have a tubular section that is generally cylindrical (i.e., internal portion). The endoscope may have a tubular section extending to the distal end and a handpiece connected to the tube and extending to the proximal end. The endoscope may have a cylindrical distal end. The body of the endoscope and the distal end of the endoscope may be different shapes. The endoscope may include one or more image sensors in a distal end region (i.e., internal portion). The one or more image sensors may be located in an external portion of the endoscope and fiber optics connected to the image sensor may transmit a signal through the internal portion to the external portion. The endoscope may include two or more image sensors. The endoscope may include an image sensor at the most distal point of the endoscope. The endoscope may include an image sensor that is located on an angle. The angle of the image sensor, viewing face, or both may be about 0°, 20°, 30°, 45°, 60°, 70°, or a combination thereof. The image sensor may provide black and white images, color images, thermal images, or a combination thereof. Preferably, the image sensor, imaging device, or both are located substantially at the distal end. The angle of the image sensor, the viewing face, or both may dictate the angle, shape, viewing cone, or a combination thereof of the endoscope.

The viewing cone may be an area of visibility of the endoscope. The viewing cone may be variable, adjustable, or both. The angle of the viewing cone may be movable. The angle of the viewing cone may be predetermined based upon the type of endoscope selected. The angle of the viewing cone may not be affected by the flow director, lumen, sheath, or a combination thereof. The location of the endoscope within the sheath may vary based upon the angle of the viewing cone. For example, the shape of the sheath may offset the endoscope to one side more or less based upon the angle of the viewing cone so that the endsoscope sheath does not interfere with the imaging of the endoscope. The viewing cone may extend outward from the distal end of the endoscope in a cone shape.

The distal end of the endoscope may function to be inserted into a patient so that a feature of interest may be viewed through minimally invasive means. The distal end of the endoscope may be the leading portion of the endoscope (i.e., the first portion that enters a patient). The distal end may function to provide washing functions, suction functions, irrigating functions, or a combination thereof that direct the irrigation fluid and suction across the viewing face of the endoscope, the lens, or both. The distal end may include one or more openings. The one or more openings may be at the very end of the distal end (e.g., a 0 degree opening). The one or more opening may be in a sidewall of the sheath, the tube, or both (e.g., 30 degrees, 45 degrees, 60 degrees, 70 degrees). The one or more openings may extend into the one or more openings so that a feature of interest may be viewed through the opening. The distal end of the endoscope may be on an opposing end of the endoscope as a proximal end. The proximal end may function to be gripped by a user. The proximal end may function to provide controls to a user. The proximal end may provide an interface for connecting other functional components such as an imaging device (e.g., a camera). The proximal end may function to provide power, sensing, suction, fluid, control, a connection point to outside devices, or a combination thereof to the distal end of the endoscope. The proximal end may be retained out of the patient and the distal end may be inserted in the patent. A shoulder may be located between the distal end and the proximal end.

The shoulder may function to prevent the proximal end from entering a patient. The shoulder may function to form a connection point with a tube of the endoscope. The shoulder may be a terminal portion of a proximal end of the endoscope. The shoulder may prevent a sheath from axially moving towards the proximal end of the endoscope. The shoulder may be located proximate to one or more light posts.

The light post may function to provide light into the endoscope. The light post may direct light into the endoscope and out of the tube of the endoscope so that a feature of interest is illuminated. The light post may provide light so that a user can see features of interests that are located in low light conditions. The one or more light posts may provide light through the endoscope, so that the visual port may be used for observing a feature of interest at a distal end of the endoscope.

The visual port may function to provide a viewing window for a user. The visual port may function to allow a user to observe a feature of interest. The visual port may function to provide an output so that an image is displayed on a monitor. The visual port may provide visual access through the endoscope to a user. The visual port may be an optical window at the proximal end that provides visual access to a viewing lens at the distal end.

The viewing lens may function to provide a window that an image sensor views through. The viewing lens may function to protect an image sensor (e.g., a camera). The viewing lens may be a cover over an image sensor. The viewing lens may be a viewing face of the endoscope and vice versa. The viewing face may be a surface of the endoscope that an image is generated through. The viewing lens may a portion of the endoscope extended into a location of interest and may be inhibited from allowing a clear image to be formed.

The sheath may function to provide one or more conduits, lumen, channels, or a combination thereof for a fluid, suction, a functional device (e.g., a cutting tool, cauterizing tool, or both), or a combination thereof to extend out of a distal end region of the sheath. The sheath may function to form all or a portion of a conduit, channel, lumen, or a combination thereof for fluid, suction, a functional device, or a combination thereof to extend out of a distal end region of the sheath. The sheath may function to provide cleaning, washing, or both of an endoscope. The sheath may provide a conduit, channel, a lumen, or a combination thereof that extends from a proximal end to a distal end. The sheath may include one or more lumen, create one or more lumen, or both. The sheath may include one or more parts that when connected together create a conduit that provides irrigation fluid, suction, a functional device, or a combination hereof to a distal end of the endoscope. The sheath may substantially mirror the shape of the endoscope. Thus, for example, if the endoscope has a circular cross-section then then sheath has a circular cross section. The sheath may function as an endoscope cleaner. The sheath may have a distal end and a proximal end with a longitudinal axis that extends therebetween.

The distal end of the sheath may function to direct irrigation fluid, suction, or both across the viewing lens, the distal end, or both of the endoscope. The proximal end of the sheath may function to create a connection with the endoscope. The proximal end may align the sheath relative to the endoscope. The proximal end of the sheath may axially align the sheath relative to the endoscope, radially align the sheath relative to the endoscope, axially align the distal ends of the sheath and the endoscope, the sheath axially relative to a light post of the endoscope, the sheath rotationally relative to a light post of the endoscope, or a combination thereof. The proximal end may receive all or a portion of the endoscope. The proximal end may contact a shoulder of the endoscope. A longitudinal axis may extend between the proximal end and the distal end of the sheath. The longitudinal axis may extend through a through hole, channel, lumen, or a combination thereof that extends the length of the sheath. The endoscope may extend within the sheath along the longitudinal axis. The longitudinal axis may extend from a connection point between the endoscope and the sheath and through a tube of the sheath.

The tube may function to receive the imaging device of the endoscope. The tube may have one or more dimples for positioning the endoscope within the sheath. The tube may include one or more dimples for creating a fluid path, a suction path, or both though the tube. The tube may be located at the distal end of the endoscope. The tube may be generally the same size and shape as the endoscope. For example, if the endoscope has a generally circular cross-section then the tube may have a generally circular cross-section.

The port may function to provide access into the tube of the sheath. The port may function to provide a fluid connection, a connection with one or more irrigation sources, a connection with one or more suction sources, one or more common lines, one or more delivery lines, or a combination thereof. The port may form a fixed connection with one or more lines so that suction, irrigation fluid, or both may be provided through the port. The port may provide direct access to the inside of the tube. The port may be configured so that one or more functional elements (e.g., a cutting tool, a cauterizing tool, or both) may gain access to the inside of the tube of the sheath, may extend out of the distal end of the sheath, or both. For example, the port may not be receive items that flow. The port may be part of a handpiece of the sheath. The port may be part of the tube, the hub, or both.

The hub may function to connect the sheath to the endoscope. The hub may function to seal the sheath to the endoscope. The hub may surround a portion of the endoscope. The hub may function to create a fluid seal with the endoscope so that irrigation fluid, suction, or both do not leak. The hub may receive a shoulder of the endoscope so that the shoulder and the hub form a fluidly sealed connection. The hub may include a collar, an arm, or both that receive all or a portion of the endoscope.

The collar may be an integral part of the hub. The collar may function to axially align, rotationally align, or both the endoscope and the sheath. The collar may form a majority of the hub (e.g., 50 percent or more, 60 percent or more, or 70 percent or more). The collar may extend partially around the light post. The collar may include one or more flares that extend proximally from the collar.

The one or more spacers may function to axially align the endoscope within the sheath. The one or more spacers may contact a shoulder of the endoscope and align the endoscope within the sheath. The spacer may contact an endoscope so that the endoscope is axially aligned within the tube. The one or more spacers may be optional. The spacer may be located proximate to one or more O-rings.

The one or more O-rings may function to form a seal between the sheath and a tube of the endoscope. The one or more O-rings may function to prevent fluid from traveling towards the proximal end of the endoscope. The one or more O-rings may function to create a seal. The one or more O-rings may be located within the hub, proximate to a collar of the hub, or both. The one or more O-rings may be made of any material that forms a seal. The one or more O-rings may create a circumferential seal, a thrust seal, or both. The one or more O-rings may be axially compressed, radially compressed, radially expanded, or a combination thereof. The one or more O-rings may include one or more through holes. The one or more O-rings may elastically deform. The one or more O-rings may be made of an elastomer, include elastic, include rubber, include a deformable material, include a deformation region, or a combination thereof. The one or more O-rings may be located proximate to a locking ring.

The one or more locking rings may lock the O-ring to the sheath, the endoscope, or both. The one or more locking rings may function to lock two or more components together. The one or more locking rings may include a through hole so that the endoscope extends through the tube and the locking ring.

A through hole may extend from a proximal end to a distal end of the sheath. A through hole may be sufficiently large so that the endoscope and fluid (e.g., irrigation fluid, suction, or both) may pass from the distal end to the proximal end of the sheath. The tube may include one or more through holes in the sheath. The through hole in the tube may open directly to a point of interest, an internal location of a patient, or both. The through hole may include one or more flow directors.

FIG. 1A illustrates a top view of sheath 90 for use with an endoscope cleaning system (not shown). The sheath 90 includes a distal end 92 and a proximal end 94. A tube 96 and hub 98 extend between the distal end 92 and the proximal end 94. The hub 98 includes a port 106 for receiving suction, an irrigation fluid, or both. The hub 98 as shown has a collar 100 that includes an optional socket 102 for receiving a light post 72 (not shown) of a corresponding device (not shown) and the socket 102 includes an undercut 104 for forming a connection with the corresponding device.

FIG. 1B illustrates an end view of the sheath 90 from the proximal end 94. The port 106 is shown extending from the hub 98 and a through hole 152 is shown extending through the tube 96 and hub 98. The socket 102 is illustrated extending through the hub 98 towards the port 106.

FIG. 1C illustrates a view of the sheath 90 from the distal end 92. A through hole 152 is shown extending through the sheath 90.

FIG. 2 illustrates a cross sectional view of the sheath 90 of FIG. 1A cut along lines A-A of FIG. 1C. The sheath 90 includes a tube 96 connected to a hub 98. The tube 96 includes a dimple 134 for aligning an endoscope (not shown) within the sheath 90. The hub 98 includes a spacer 128 between an end of the tube 96 and a mating surface of the hub 98. An O-ring 130 is located in the hub proximate to a locking ring 132 for creating connection between the hub 98 and an endoscope (not shown). The tube 96 includes a dimple 134 along the longitudinal axis of the tube 90.

FIG. 3 illustrates an endoscope 60 extending into a sheath 90. The endoscope 60 includes a proximal end 64 including a visual port 74. The visual port 74 allows a user to view locations of interest located within the viewing cone 78 at the distal end 62 of the endoscope 60 (e.g., a 0 degree endoscope). The endoscope 60 includes a distal end 62 that extends to a distal end 92 of a sheath 90. The sheath 90 includes a tube 96 extending from a distal end 92 to a hub 98. The hub 98 includes a port for receiving suction, an irrigation fluid, or both. The hub 98 terminates at a proximal end 94 that receives a shoulder 70 of a light port 72.

Figure 4:
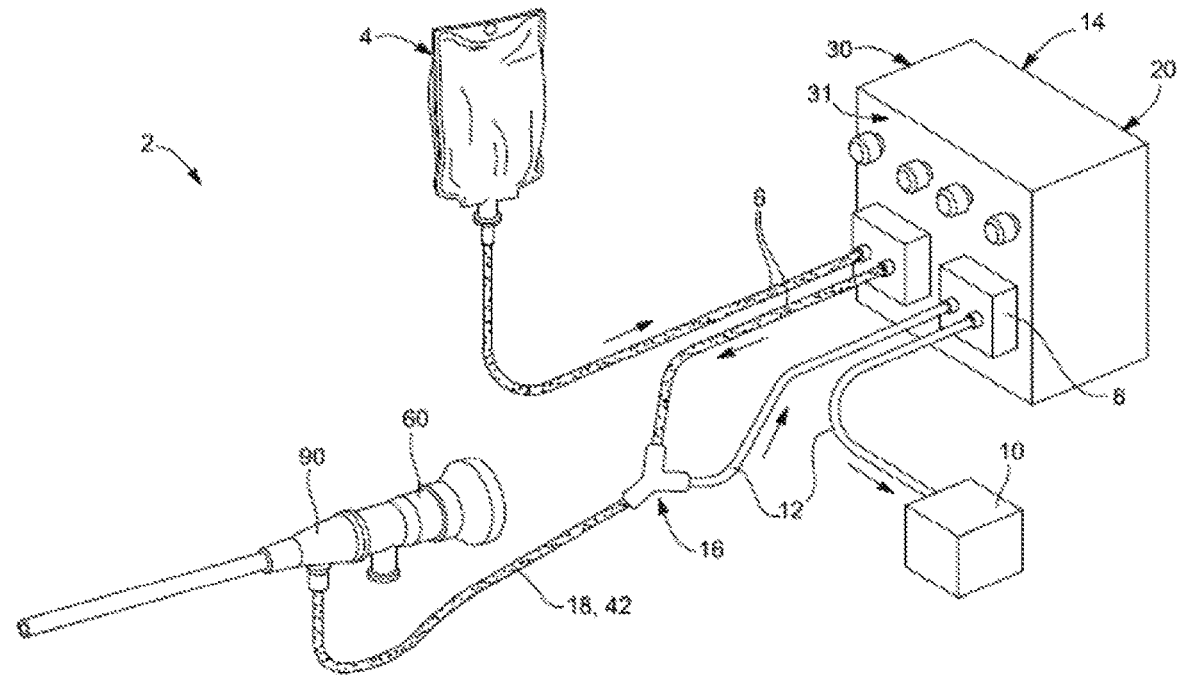
FIG. 4 illustrates a system including a sheath.

FIG. 4 illustrates an endoscope cleaning system 2. The endoscope cleaning system 2 includes an irrigation source 4 connected to an irrigation line 6 that is connected to a control module 30 having a pump 14 for controlling flow of irrigation fluid between the irrigation source 4 and a sheath 90. The control module 30 includes a power source 20 and a controller and/or microprocessor (not shown) that is in communication with a user interface 31 for controlling the control module 30. The system 2 includes a suction source 10 that is connected to the control module 30. The control module 30 includes a valve 8 that controls suction through the suction line 6. The valve 8 for controls suction between the suction source 10 and the sheath 90 so that suction may be turned off during all or portion of the application cycle of the irrigation fluid. The irrigation line 6 and the suction line 12 are connected together at a common fitting 16 that connects the irrigation line 6 and the suction line 12 to a common line 18/delivery line 42 for supplying a fluid or suction to the sheath 90 for cleaning an endoscope (not shown). The common line 18/delivery line 42 are long enough so that during the suction cycle the common line 18/deliver line 42 is not evacuated of fluid.

Figure 5:
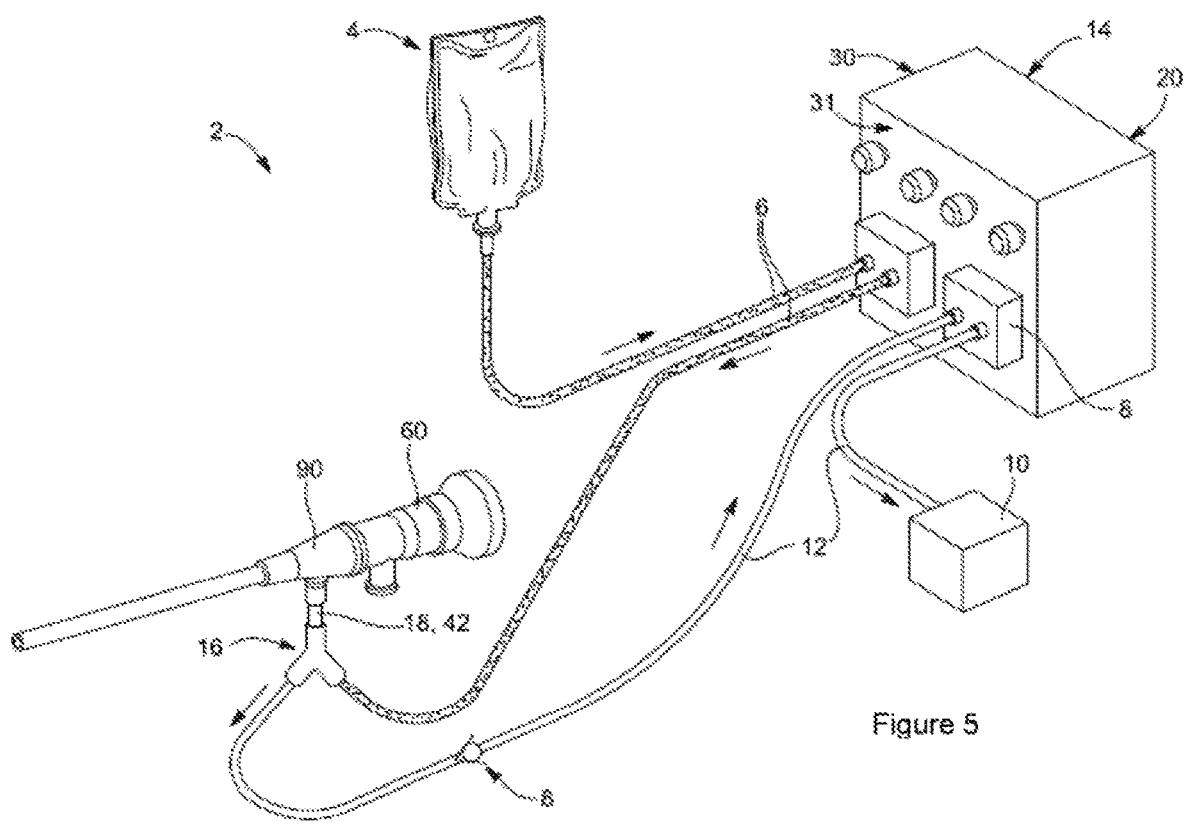
FIG. 5 illustrates another system including a sheath of the teachings herein.

FIG. 5 illustrates a control module 30 that includes a pump 14, a power source 20, a user interface 31, and one or more valves 8. The irrigation source 4 is gravity fed into the pump 14 and then the pump 14 sends fluid through the irrigation line 6 to the sheath 90 so that the sheath 90 washes the endoscope 60. The suction source 10 is connected to a valve 8 of the control module 30 that controls suction being drawn through the suction lines 12. Both the irrigation lines 6 and the suction lines 12 are connected to a common fitting 16 and a single common line 18/delivery line 42 extend from the common fitting 16 to the sheath 90. The common line 18/delivery line 42 is short enough so that all of the fluid is evacuated when the suction cycle is initiated. The suction line 12 may include a valve 8 that is a passive check valve to prevent irrigation fluid from being forced into the suction line.

Figure 6:
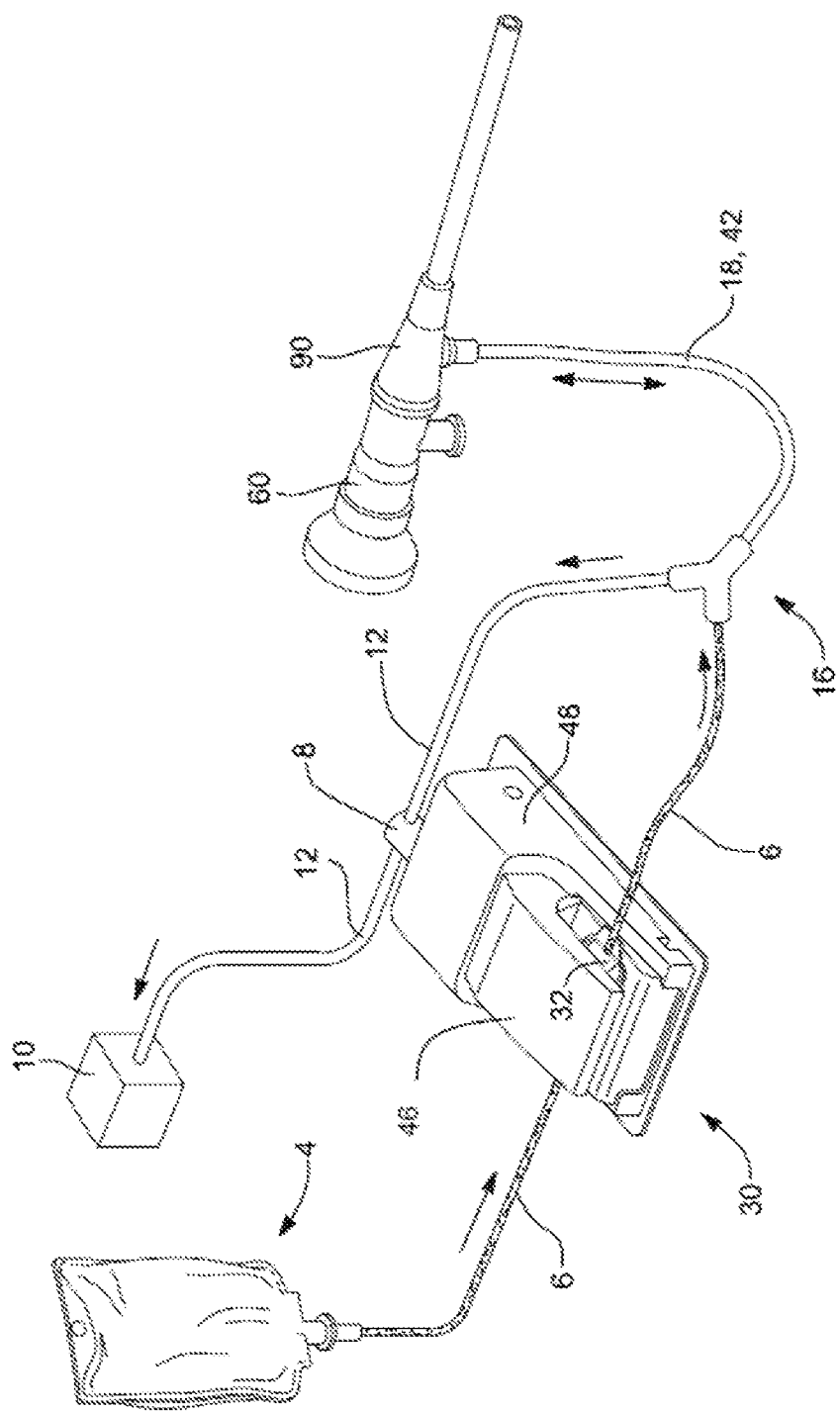
FIG. 6 illustrates a system including a foot control module.

FIG. 6 illustrates a system including a control module 30 that controls the flow of irrigation fluid and suction through the system. An irrigation source 4 is connected to a resilient reservoir 32 by an irrigation line 6. The resilient reservoir 32 is located between an actuation member 47 and a base 48 so that upon movement of the actuation member 47 the resilient reservoir 32 is compressed and irrigation fluid is moved into the irrigation line 6 towards the common fitting 16 and from the common fitting 16 into the common line 18/delivery line 42 so that the irrigation fluid is supplied to the sheath 90 to wash the endoscope 60. At some predetermined time after movement of the actuation member 47 the control module 30 will activate suction to be applied. The valve 8 will actuate so that suction moves from the endoscope 90 through the common line 18/delivery line 42 past the common fitting 16 and into the suction line 12. The suction line 12 extends through the valve 8 and into the suction source 10.

Figure 7:
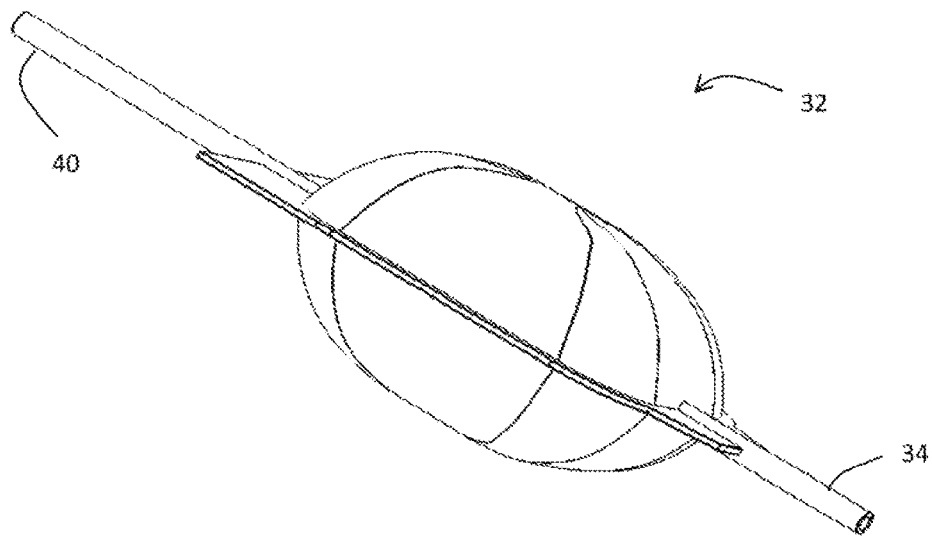
FIG. 7 illustrates a resilient reservoir.

FIG. 7 illustrates a resilient reservoir 32. The resilient reservoir 32 includes and an entrance port 34 for supplying fluid to the resilient reservoir 32 and an exit port 40 that supplies fluid to a sheath (not shown).

Figure 8:
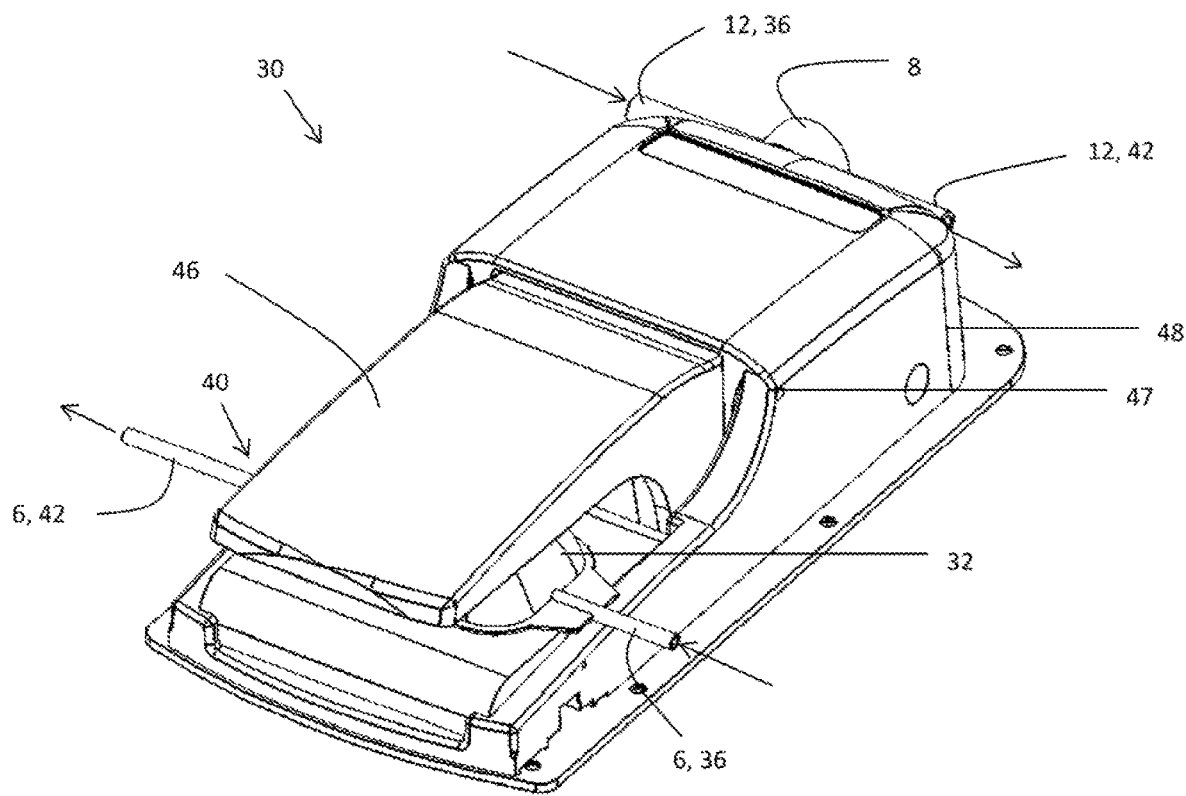
FIG. 8 illustrates a control module including a resilient reservoir.

FIG. 8 illustrates a control module 30. The control module 30 includes an actuation member 46 that extends over a resilient reservoir 32 and assists in controlling the flow of fluid from the resilient reservoir 32 to a sheath 90 (not shown). As illustrated, fluid is fed into the resilient reservoir 32 via a supply line 36/irrigation line 6 that extends from an irrigation source 4 (not shown). When the actuation member 46 is actuated the actuation member 46 rotates about a pivot point 47 so that the actuation member 46 compresses the resilient reservoir 32 between the actuation member 46 and a base 48 moving fluid out of the exit port 40 through a delivery line 42/irrigation line 6. Movement of the actuation member 46 triggers a predetermined response where after a predetermined amount of time the valve 8 is actuated so that suction is applied though the suction line 12 from the supply line 36 side through the valve 8 and to the delivery line 42 side.

Figure 9:
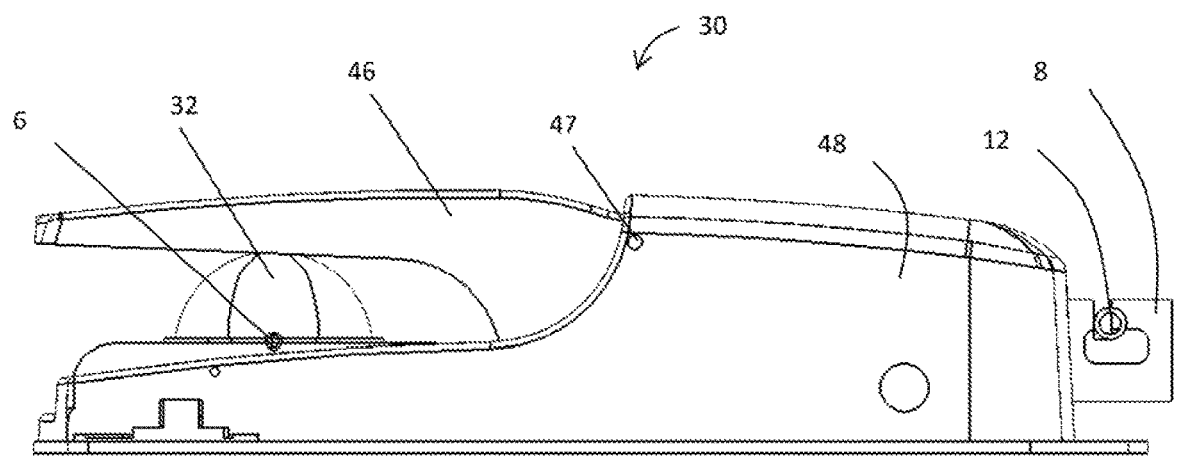
FIG. 9 illustrates a side view of a control module.

FIG. 9 illustrates a side view of a control module 30. The control module 30 includes an irrigation line 6 that is connected to a resilient reservoir 32. The resilient reservoir 32 is compressed by an actuation member 46 that rotates about a pivot 47 to expel fluid. The actuation member 46 is connected to the base 48 by the pivot 47 and moves relative to the base 48. A suction line 12 extends through a valve 8 that controls the flow of suction in the system.

Figure 10:
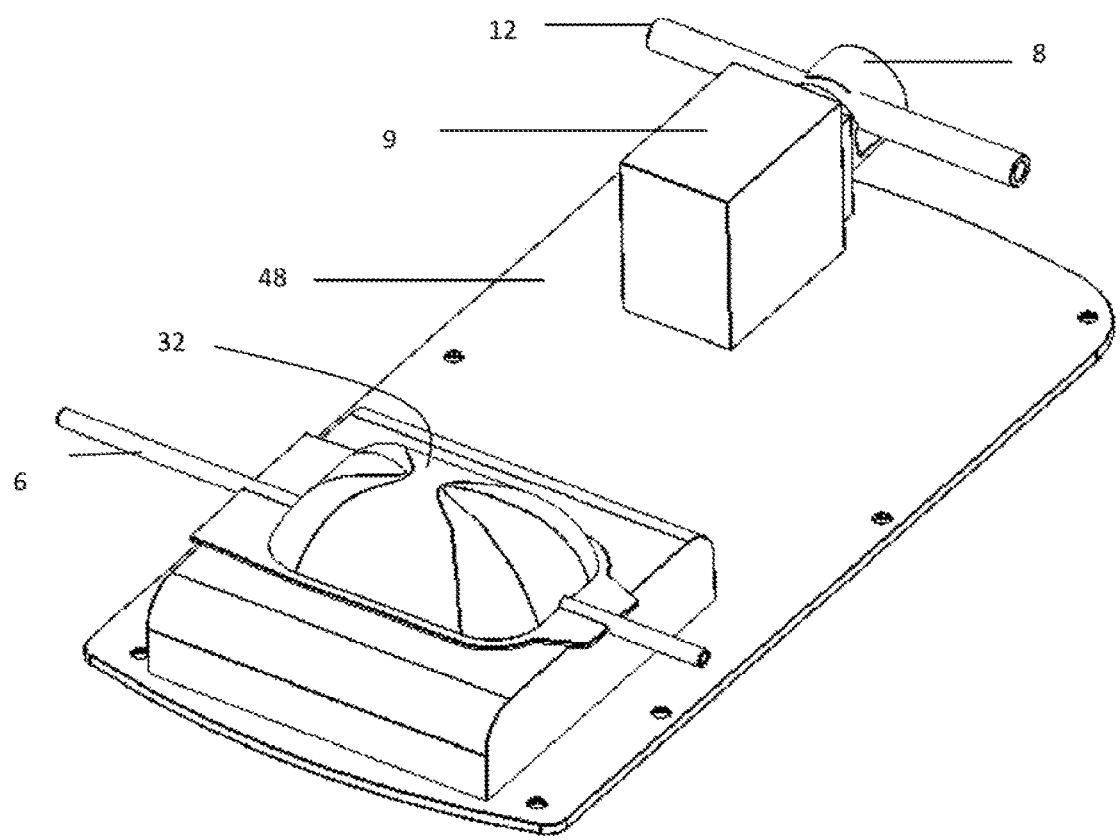
FIG. 10 illustrates a perspective view of a control module with a cover removed from the base portion.

FIG. 10 illustrates a perspective view of a cover of the base 48 removed. As illustrates the resilient reservoir 32 rests in a cradle and includes an irrigation line 6 extending from each side. The suction line 12 extends through a valve 8 which is controlled by an electrical controller 9 during movement of the actuation member (not shown).

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A control module comprising:
a) a base;
b) an actuation member;
c) a valve configured to be operably connected to an irrigation line, a suction line, and an endoscope sheath; and
d) a resilient reservoir;
wherein the actuation member is configured to be capable of controlling both the suction line and the irrigation line during an operation; and wherein movement of the actuation member compresses the resilient reservoir to move irrigation fluid from the resilient reservoir to the endoscope sheath to assist in cleaning an endoscope.

2. The control module of claim 1, wherein the resilient reservoir is configured to be connectable to an irrigation source.

3. The control module of claim 1, wherein compression of the resilient reservoir initiates movement of the valve so that the valve opens the suction line that is connected to a suction source.

4. The control module of claim 1, wherein the actuation member is configured to evenly apply compression to the resilient reservoir to create pressure to move irrigation fluid from the resilient reservoir.

5. The control module of claim 1, wherein the resilient reservoir expands when compression of the resilient reservoir is complete so that irrigation fluid ceases to be applied and releases the valve so that suction is applied to the endoscope sheath.

6. The control module of claim 1, wherein the actuation member is movable relative to the base.

7. The control module of claim 1, wherein the actuation member is a foot pedal.

8. The control module of claim 1, wherein the resilient reservoir is located between the actuation member and the base.

9. The control module of claim 1, wherein movement of the actuation member triggers a response where after a predetermined amount of time, the valve is actuated so that suction is applied through the suction line.

10. The control module of claim 1, wherein the suction line extends through the valve.

11. The control module of claim 1, wherein the suction line is generally parallel to the irrigation line at the base.

12. The control module of claim 11, wherein the resilient reservoir comprises an entrance port for supplying fluid to the resilient reservoir and an exit port for supplying the fluid to the endoscope sheath, and the entrance port and the export are aligned on opposite sides of the resilient reservoir.

13. The control module of claim 1, wherein the resilient reservoir is located at one end of the base and the valve is located an opposite end of the base.

14. A control module comprising
a) a base;
b) an actuation member;
c) a valve configured to be operably connected to an irrigation line, a suction line, and an endoscope sheath,
d) a reservoir
wherein the actuation member is configured to be capable of controlling both the suction line and the irrigation line during an operation,
wherein movement of the actuation member compresses the reservoir to move irrigation fluid from the reservoir to the endoscope sheath, and
wherein the compression of the reservoir initiates movement of the valve so that the valve opens the suction line.

15. The control module of claim 14, wherein the reservoir is configured to expand when compression of the reservoir is complete so that the irrigation fluid ceases to be applied to the endoscope and releases the valve so that suction is applied to the endoscope sheath.

16. The control module of claim 14, wherein movement of the actuation member triggers a response where after a predetermined amount of time, the valve is actuated so that suction is applied through the suction line.

17. The control module of claim 15, wherein movement of the actuation member triggers a response where after a predetermined amount of time, the valve is actuated so that suction is applied through the suction line.

18. The control module of claim 14, wherein the actuation member is a foot pedal.

19. A control module comprising:
a) a base;
b) an actuation member;
c) a valve configured to be operably connected to an irrigation line, a suction line, and an endoscope sheath; and
d) a resilient reservoir;
wherein the actuation member is configured to be capable of controlling both the suction line and the irrigation line during an operation; and
wherein the resilient reservoir expands when compression of the resilient reservoir is complete so that irrigation fluid ceases to be applied and releases the valve so that suction is applied to the endoscope sheath.

* * * * *